US008039505B2

(12) United States Patent
Trede

(10) Patent No.: US 8,039,505 B2
(45) Date of Patent: Oct. 18, 2011

(54) COMPOUNDS FOR MODULATING T-CELLS

(75) Inventor: Nikolaus S. Trede, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 387 days.

(21) Appl. No.: 12/101,690

(22) Filed: Apr. 11, 2008

(65) Prior Publication Data
US 2008/0293739 A1 Nov. 27, 2008

Related U.S. Application Data

(60) Provisional application No. 60/922,908, filed on Apr. 11, 2007.

(51) Int. Cl.
*A61K 38/00* (2006.01)
*A61K 31/496* (2006.01)
*A61K 31/426* (2006.01)

(52) U.S. Cl. .................. 514/412; 514/228.5; 514/264.1; 514/353; 514/339; 514/217

(58) Field of Classification Search ............... 514/228.5, 514/264.1, 412, 353, 339, 245.01, 255.01, 514/254
See application file for complete search history.

(56) References Cited

U.S. PATENT DOCUMENTS
2005/0119177 A1* 6/2005 Bar-Or et al. .................... 514/12

OTHER PUBLICATIONS

Autoimmune diseases document, 2005, retrieved from the web on Jun. 21, 2010, URL: http://web.archive.org/web/20051202040221/http://www.labtestsonline.org.*
Bowman, CME Journal, Jan. 15, 1981, vol. 124, pp. 129-142.*
Ackermann et al., "Zebrafish: a genetic model for vertebrate organogenesis and human disorders," *Front Biosci* 8:d1227-1253 (2003).
Aster, "Deregulated NOTCH signaling in acute T-cell lymphoblastic leukemia/lymphoma: new insights, questions, and opportunities," *Int J Hematol* 82:295-301 (2005).
Bennett et al., "Prospective phase 1/2 study of rituximab in childhood and adolescent chronic immune thrombocytopenic purpura," *Blood* 107:2639-2642 (2006).
Berube et al., "Apoptosis caused by p53-induced protein with death domain (PIDD) depends on the death adapter protein RAIDD," *Proc Natl Acad Sci U S A* 102:14314-14320 (2005).
Chhabra et al., "Activation-induced cell death of human melanoma specific cytotoxic T lymphocytes is mediated by apoptosis-inducing factor," *Eur J Immunol* 36:3167-3174 (2006).
Chipuk et al., "Dissecting p53-dependent apoptosis," *Cell Death Differ* 13:994-1002 (2006).
Clift et al., "Marrow transplantation for CML: the Seattle experience," *Bone Marrow Transplant* 17 Suppl 3:S1-3 (1996).
Cvetkovic et al., "Rituximab: a review of its use in non-Hodgkin's lymphoma and chronic lymphocytic leukaemia," *Drugs* 66:791-820 (2006).

(Continued)

*Primary Examiner* — Jeffrey S Lundgren
*Assistant Examiner* — Savitha Rao
(74) *Attorney, Agent, or Firm* — Ballard Spahr LLP

(57) ABSTRACT

Disclosed are compounds and compositions that modulate T-cells. Such compounds can be used to treat T-cell mediated disease like T-ALL, rheumatoid arthritis, multiple sclerosis, and graft-vs-host disease (GvHD), to name but a few. The compounds have a general structure as shown in Formula I.

$$Ar^1\text{-L-}Ar^2 \qquad \qquad I$$

wherein $Ar^1$ and $Ar^2$, are independent of one another, a substituted aryl, unsubstituted aryl, substituted heteroaryl, or unsubstituted heteroaryl; and L is a bond or a linker spanning two, three, four, or five atoms.

14 Claims, 11 Drawing Sheets

OTHER PUBLICATIONS

Druker et al., "Five-year follow-up of patients receiving imatinib for chronic myeloid leukemia," *N Engl J Med* 355:2408-2417 (2006).
Druker et al., "Effects of a selective inhibitor of the Abl tyrosine kinase on the growth of Bcr-Abl positive cells," *Nat Med* 2:561-566 (1996).
Esteve et al., "Rho-regulated signals induce apoptosis in vitro and in vivo by a p53-independent, but Bcl2 dependent pathway," *Oncogene* 17:1855-1869 (1998).
Goldberg et al., "Childhood T-cell acute lymphoblastic leukemia: the Dana-Farber Cancer Institute acute lymphoblastic leukemia consortium experience," *J Clin Oncol* 21:3616-3622 (2003).
Gozuacik et al., "Autophagy and cell death," *Curr Top Dev Biol* 78:217-245 (2007).
Grabher et al., "Notch 1 activation in the molecular pathogenesis of T-cell acute lymphoblastic leukaemia," *Nat Rev Cancer* 6:347-359 (2006).
Guo et al., "β-Catenin stabilization stalls the transition from Double-Positive to Single Positive stage and predisposes thymocytes to malignant transformation," *Blood* (2007).
Hatanaka et al., "Photoaffinity labeling in drug discovery and developments: chemical gateway for entering proteomic frontier," *Curr Top Med Chem* 2:271-288 (2002).
Heidel et al., "Addition of rituximab to standard therapy improves response rate and progression-free survival in relapsed or refractory thrombotic thrombocytopenic purpura and autoimmune haemolytic anaemia," *Thromb Haemost* 97:228-233 (2007).
Holler et al., "Fas triggers an alternative, caspase-8-independent cell death pathway using the kinase RIP as effector molecule," *Nat Immunol* 1:489-495 (2000).
Jaattela et al., "Caspase-independent cell death in T lymphocytes," *Nat Immunol* 4:416-423 (2003).
Langenau et al., "In vivo tracking of T cell development, ablation, and engraftment in transgenic zebrafish," *Proc Natl Acad Sci U S A* 101:7369-7374 (2004).
Langenau et al., "Suppression of apoptosis by bcl-2 overexpression in lymphoid cells of transgenic zebrafish," *Blood* 105:3278-3285 (2005).
Langenau et al., "Myc-induced T cell leukemia in transgenic zebrafish," *Science* 299:887-890 (2003).
Lin et al., "Pidd, a new death-domain-containing protein, is induced by p53 and promotes apoptosis," *Nat Genet* 26:122-127 (2000).
Murphey et al., "A chemical genetic screen for cell cycle inhibitors in zebrafish embryos," *Chem Biol Drug Des* 68:213-219 (2006).
Nesbit et al., "Chemotherapy for induction of remission of childhood acute myeloid leukemia followed by marrow transplantation or multiagent chemotherapy: a report from the Childrens Cancer Group," *J Clin Oncol* 12:127-135 (1994).
Newton et al., "Effects of a dominant interfering mutant of FADD on signal transduction in activated T cells," *Curr Biol* 11:273-276 (2001).
O'Connor et al., "CD95 (Fas/APO-1) and p53 signal apoptosis independently in diverse cell types," *Cancer Res* 60:1217-1220 (2000).
Oeffinger et al., "Chronic health conditions in adult survivors of childhood cancer," *N Engl J Med* 355:1572-1582 (2006).
Peterson et al., "Small molecule developmental screens reveal the logic and timing of vertebrate development," *Proc Natl Acad Sci U S A* 97:12965-12969 (2000).
Peterson et al., "Chemical suppression of a genetic mutation in a zebrafish model of aortic coarctation," *Nat Biotechnol* 22:595-599 (2004).
Randolph, "Acute promyelocytic leukemia (AML-M3)—Part 1: Pathophysiology, clinical diagnosis, and differentiation therapy," *Clin Lab Sci* 13:98-105 (2000).
Randolph, "Acute promyelocytic leukemia (AML-M3)—Part 2: Molecular defect, DNA diagnosis, and proposed models of leukemogenesis and differentiation therapy," *Clin Lab Sci* 13:106-116 (2000).
Reiter et al., "Chemotherapy in 998 unselected childhood acute lymphoblastic leukemia patients. Results and conclusions of the multicenter trial ALL-BFM 86," *Blood* 84:3122-3133 (1994).
Schmitt et al., "Dissecting p53 tumor suppressor functions in vivo," *Cancer Cell* 1:289-298 (2002).
Seddon et al., "TCR signals mediated by Src family kinases are essential for the survival of naive T cells," *J Immunol* 169:2997-3005 (2002).
Shepard et al., "A zebrafish bmyb mutation causes genome instability and increased cancer susceptibility," *Proc Natl Acad Sci U S A* 102:13194-13199 (2005).
Spring, "Chemical genetics to chemical genomics: small molecules offer big insights," *Chem Soc Rev* 34:472-482 (2005).
Stegmaier et al., "Gefitinib induces myeloid differentiation of acute myeloid leukemia," *Blood* 106:2841-2848 (2005).
Stern et al., "Small molecules that delay S phase suppress a zebrafish bmyb mutant," *Nat Chem Biol* 1:366-370 (2005).
Strasser et al., "DNA damage can induce apoptosis in proliferating lymphoid cells via p53-independent mechanisms inhibitable by Bcl-2," *Cell* 79:329-339 (1994).
Tejeda et al., "Growth inhibitory effect of the somatostatin structural derivative (TT-232) on leukemia models," *Anticancer Res* 25:325-330 (2005).
Tolomeo et al., "Drug resistance and apoptosis in cancer treatment: development of new apoptosis-inducing agents active in drug resistant malignancies," *Curr Med Chem Anticancer Agents* 2:387-401 (2002).
Trede et al., "The use of zebrafish to understand immunity," *Immunity* 20:367-379 (2004).
Trede et al., "Organ development in zebrafish linked to network of coregulated splicing factors," *Proc. Natl. Acad. Sci.* in press (2007).
Trede N., "Modeling and treating immune-mediated diseases using a transgenic line of zebrafish," presented Apr. 8, 2006 at Thymoz Meeting International Workshop on T Lymphocytes, Heron Island, Australia (abstract).
Wahlstrom et al., "Structural model of the regulatory domain of smooth muscle heavy meromyosin," *J Biol Chem* 278:5123-5131 (2003).
Walensky et al., "Activation of apoptosis in vivo by a hydrocarbon-stapled BH3 helix," *Science* 305:1466-1470 (2004).
Wang et al., "Lymphoid potential of primitive bone marrow progenitors evaluated in vitro," *Ann N Y Acad Sci* 1044:210-219 (2005).
Wang et al., "Distinct roles of IL-7 and stem cell factor in the OP9-DL1 T-cell differentiation culture system," *Exp Hematol* 34:1730-1740 (2006).
Weng et al., "Activating mutations of NOTCH1 in human T cell acute lymphoblastic leukemia," *Science* 306:269-271 (2004).
Weng et al., "c-Myc is an important direct target of Notch1 in T-cell acute lymphoblastic leukemia/lymphoma," *Genes Dev* 20:2096-2109 (2006).
Zon et al., "In vivo drug discovery in the zebrafish," *Nat Rev Drug Discov* 4:35-44 (2005).

\* cited by examiner

| Treatment | Mouse ID | WBC (G/l) | RBC (T/l) | Hb (g/l) | Hct (l/l) | Plt (G/l) | Neut (%) | Lymph (%) | Eosi (%) | Mono (%) | Baso (%) |
|---|---|---|---|---|---|---|---|---|---|---|---|
| Vehicle Control | 306 | 13.6 | 10.1 | 158 | 0.50 | 1103 | 9.1 | 94.6 | 2.5 | 2.3 | 0.50 |
| | 307 | 10.0 | 10.3 | 164 | 0.53 | 1232 | 17.4 | 75.3 | 3.5 | 2.0 | 0.60 |
| | 308 | 9.5 | 10.1 | 156 | 0.51 | 1162 | 13.5 | 78.4 | 3.2 | 3.1 | 0.50 |
| | 309 | 14.5 | 10.1 | 157 | 0.52 | 948 | 9.7 | 80.8 | 1.9 | 6.3 | 0.50 |
| | 310 | 12.4 | 9.6 | 159 | 0.51 | 920 | 10.8 | 78.1 | 2.1 | 7.5 | 0.60 |
| | 311[a] | 33.5 | 8.1 | 103 | 0.36 | 1606 | 60.8 | 35.2 | 1.3 | 0.6 | 0.20 |
| | Mean | 12.0 | 10.0 | 158.8 | 0.51 | 1073.0 | 12.1 | 79.4 | 2.64 | 4.24 | 2.54 |
| | SD | 2.2 | 0.3 | 3.1 | 0.01 | 135.2 | 3.4 | 3.5 | 0.69 | 2.50 | 0.05 |
| Formulation | 300 | 7.7 | 10.6 | 169 | 0.52 | 761 | 18.4 | 71.6 | 3.9 | 4.7 | 0.70 |
| | 301 | 5.1 | 9.7 | 150 | 0.48 | 1096 | 28.7 | 52.4 | 1.4 | 16.1 | 1.4 |
| | 302 | 6.3 | 10.5 | 165 | 0.54 | 1149 | 15.2 | 69.5 | 2.4 | 12.0 | 0.30 |
| | 303 | 7.2 | 10.7 | 157 | 0.49 | 1143 | 14.2 | 74.8 | 3.1 | 6.4 | 0.40 |
| | 304 | 6.4 | 10.9 | 175 | 0.56 | 1093 | 14.9 | 71.6 | 2.5 | 9.7 | 0.40 |
| | 305 | 11.5 | 9.8 | 153 | 0.50 | 1252 | 8.1 | 86.3 | 1.1 | 3.3 | 0.40 |
| | Mean | 7.4* | 10.3 | 160.7 | 0.523 | 1090.7 | 16.6 | 71.0 | 2.40 | 8.70 | 0.43 |
| | SD | 2.2 | 0.5 | 10.4 | 0.03 | 172.4 | 6.8 | 10.9 | 1.04 | 4.84 | 0.14 |

FIG. 7A

| Treatment | Mouse ID | WBC (G/l) | RBC (T/l) | Hb (g/l) | Hct (l/l) | Plt (G/l) | Neut (%) | Lymph (%) | Eosi (%) | Mono (%) | Baso (%) |
|---|---|---|---|---|---|---|---|---|---|---|---|
| Vehicle Control | 318 | 7.1 | 9.5 | 154 | 0.51 | 1177 | 12.6 | 82.9 | 0.7 | 2.4 | 0.30 |
| | 319 | 10.1 | 9.5 | 141 | 0.45 | 1210 | 30.1 | 63.6 | 1.3 | 3.3 | 0.30 |
| | 320 | 11.5 | 10.1 | 145 | 0.48 | 1164 | 25.8 | 66.1 | 2.4 | 4.1 | 0.30 |
| | 321 | 3.7 | 9.8 | 156 | 0.50 | 874 | 24.3 | 69.1 | 0.3 | 5.2 | 0.20 |
| | 322 | 6.3 | 9.8 | 141 | 0.48 | 917 | 27.6 | 62.2 | 1.0 | 7.8 | 0.30 |
| | 323 | 8.9 | 8.9 | 142 | 0.46 | 925 | 46.2 | 49.0 | 0.5 | 3.4 | 0.30 |
| | Mean | 7.9 | 9.7 | 146.5 | 0.48 | 1044.5 | 27.8 | 65.5 | 1.03 | 4.37 | 0.28 |
| | SD | 2.8 | 0.5 | 6.8 | 0.02 | 165.1 | 10.9 | 11.0 | 0.76 | 1.92 | 0.04 |
| Formulation | 312 | 6.0 | 10.0 | 153 | 0.49 | 769 | 13.1 | 70.0 | 1.6 | 4.7 | 0.30 |
| | 313 | 9.0 | 10.6 | 163 | 0.51 | 852 | 14.3 | 73.6 | 2.4 | 8.6 | 0.30 |
| | 314 | 13.3 | 10.4 | 160 | 0.52 | 564 | 11.2 | 82.8 | 2.2 | 2.2 | 0.60 |
| | 315 | 12.8 | 9.9 | 160 | 0.51 | 528 | 25.7 | 66.7 | 2.2 | 4.3 | 0.20 |
| | 316 | 1.5 | 8.5 | 129 | 0.43 | 790 | 39.7 | 48.3 | 2.1 | 7.1 | 0.40 |
| | 317 | 6.8 | 10.3 | 151 | 0.49 | 1098 | 31.4 | 62.8 | 0.8 | 3.1 | 0.20 |
| | Mean | 8.2 | 10.0 | 152.3 | 0.49 | 766.8* | 22.6 | 67.4 | 1.88 | 6.57 | 0.33 |
| | SD | 4.5 | 0.8 | 12.2 | 0.03 | 207.7 | 11.6 | 11.6 | 0.59 | 4.41 | 0.15 |

FIG. 7B

COMPOUNDS FOR MODULATING T-CELLS

CROSS REFERENCE TO RELATED APPLICATIONS

This application claims the benefit of priority to U.S. Provisional Application No. 60/922,908, filed Apr. 11, 2007. U.S. Provisional Application No. 60/922,908 is incorporated by reference herein in its entirety.

BACKGROUND

Acute lymphocytic leukemia (ALL) is the most common cancer of childhood. This disease is caused by developmental arrest and clonal expansion of a transformed, immature lymphocyte. Until recently all leukemias carried a poor prognosis. What sets ALL apart from other leukemias such as acute and chronic myeloid leukemias (AML and CML) is the fact that, with rare exceptions, a leukemic stem cell in ALL has so far not been convincingly demonstrated. The stem cell characteristics of the malignantly transformed cell underlying CML make this disease a treatment challenge because complete eradication of the leukemic stem cell would entail destruction of all hematopoietic stem cells. This may explain why great strides have been made in the treatment of ALL with multi-agent chemotherapy alone, while (with rare exceptions, e.g., M3 AML) that is not the case for AML and CML, where bone marrow transplantation is superior to chemotherapy alone (Nesbit et al., *J Clin Oncol* 12:127-135, 1994; Clift and Storb. *Bone Marrow Transplant* 17 Suppl 3:S1-3, 1996). However, ALL treatment comes at a high price in the form of severe side effects, especially so in the case of T-cell acute lymphocytic leukemia (T-ALL), which is the most difficult form of childhood ALL to treat (Goldberg et al., *J Clin Oncol* 21:3616-3622, 2003).

The reason why side effects from conventional chemotherapy are so common is based on the mechanism of action of most chemotherapeutic agents: they interfere with various phases of the cell cycle (Oeffinger et al., *N Engl J Med* 355:1572-1582, 2006). Therapeutic benefit comes from the fact that leukemic cells cycle much faster than cells from other body tissues, so that the former are predominantly affected. However, any cell in the body that divides during chemotherapy will also be affected, which leads to short term (hair loss, vomiting) and long term (weakening of bones, short stature, infertility, learning deficits, heart disease and secondary cancers) side effects. Therefore, the future of successful leukemia treatment lies in more targeted therapy that affects only leukemic cells (or the lineage they are derived from) to reduce toxic side effects. Several strategies have been employed to this effect.

For Philadelphia chromosome (t9;22) positive CML, a specific inhibitor, Gleevec, of the BCR/ABL tyrosine kinase was developed (Druker et al., *Nat Med* 2:561-566, 1996). While not curative, Gleevec has been successfully applied in clinical practice (Druker et al., *N Engl J Med* 355:2408-2417, 2006) to induce prolonged remissions, and is well tolerated. In AML, the success of the differentiation-inducing effect of all trans retinoic acid (ATRA) in the treatment of M3 AML has led to the search for FDA approved drugs that induce differentiation of AML cell lines (Randolph, *Clin Lab Sci* 13:106-116, 2000; Randolph, *Clin Lab Sci* 13:98-105, 2000). This resulted in the identification of compounds such as iressa (Stegmaier et al., *Blood* 106:2841-2848, 2005)—not previously known or suspected to have anti-AML activity—that can now be tested for efficacy in the treatment of AML.

Recent research in T-ALL revealed a surprisingly high number of cases where Notch-1 is deregulated (reviewed in Grabher et al., *Nat Rev Cancer* 6:347-359, 2006; Weng et al., *Science* 306:269-271, 2004), a pathway that also includes c-myc activation (Weng et al., *Genes Dev* 20:2096-2109, 2006). This has led to first attempts to treat patients with Notch-1 deregulated T-ALL with gamma secretase inhibitors (reviewed in (Aster, *Int J Hematol* 82:295-301, 2005). While roughly half of T-ALL patients appear have Notch-1 pathway deregulation, others have defective wnt-signaling (Guo et al., *Blood* in-press, 2007) or other, unknown genetic aberrations that lead to leukemogenesis.

When the molecular target, such as a deregulated proto-oncogene, is unknown, an alternative approach comprises the ablation of the entire hematopoietic lineage that the transformed leukemic cell is derived from. This approach is best exemplified by the use of the anti-CD20 monoclonal antibody Rituximab. In non-Hodgkin lymphoma, expression of the surface marker CD20 has been exploited successfully for elimination of lymphoma cells along with almost all B cells using Rituximab (Cvetkovic Perry. *Drugs* 66:791-820, 2006). Rituximab is also effective in treating non-malignant, autoimmune hematologic diseases (Bennett et al., *Blood* 107:2639-2642, 2006; Heidel et al., *Thromb Haemost* 97:228-233, 2007). Downsides of antibody treatments are side effects and high cost.

An additional treatment alternative is the use of small chemical molecules that are capable of eliminating a subset of hematopoietic cells. Small molecule activity can be detected in assays for functional inhibition of a particular molecular target (e.g., Gleevec against kinase activity of BCR/ABL), or in screens that interrogate a particular pathway or developmental process. The latter approach is particularly powerful if molecular targets affected in a disease or developmental process is unknown (Peterson et al., *Proc Natl Acad Sci USA* 97:12965-12969, 2000).

What are needed in the art are new T-cell specific drugs that can improve efficacy of treatment and reduce side effects from treatment in patients with T-cell mediated diseases like T-ALL. As the molecular target in a large number of patients with T-ALL has not been identified, an unbiased, novel approach to the therapy of this disease is needed. As such, a small molecule library of compounds has been screened in live, transgenic zebrafish and in vitro against human T-ALL cell lines. These compounds, including derivatives and pharmaceutical salts thereof, are disclosed herein, as are methods of making and using such compositions.

SUMMARY

In accordance with the purposes of the disclosed materials, compounds, compositions, articles, and methods, as embodied and broadly described herein, the disclosed subject matter, in one aspect, relates to compounds and compositions and methods for preparing and using such compounds and compositions. In a further aspect, disclosed herein are compounds and compositions that modulate T-cells. In still a further aspect, disclosed herein are methods of using such compounds and compositions in a T-cell mediated disease, like T-ALL, rheumatoid arthritis, multiple sclerosis, and graft-vs-host disease (GvHD), to name but a few.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF FIGURES

The accompanying figures, which are incorporated in and constitute a part of this specification, illustrate several aspects described below.

FIGS. 7 and 8 refer to testing in mice of compound 3. These tests were carried out by Advinus Therapeutics (Bangalore, India). FIG. 7A is a table of hematological values following intraveneous administration of 1H-indole-3-carbaldehyde quinoline-8-ylhydrazone (Compound C3) formulation (3 mg/kg) and vehicle in male Swiss Albino mouse. FIG. 7B is a table of hematological values following oral administration of 1H-indole-3-carbaldehyde quinoline-8-ylhydrazone formulation (3 mg/kg) and vehicle in male Swiss Albino mouse.

FIG. 8 is a plasma concentration-time profile (Mean ±SD; N=3) of 1H-indole-3-carbaldehyde quinolin-8-ylhydrazone in male Swiss Albino mouse following intravenous bolus (3 mg/kg) and oral solution (15 mg/kg) administration.

DETAILED DESCRIPTION

Figure 1:
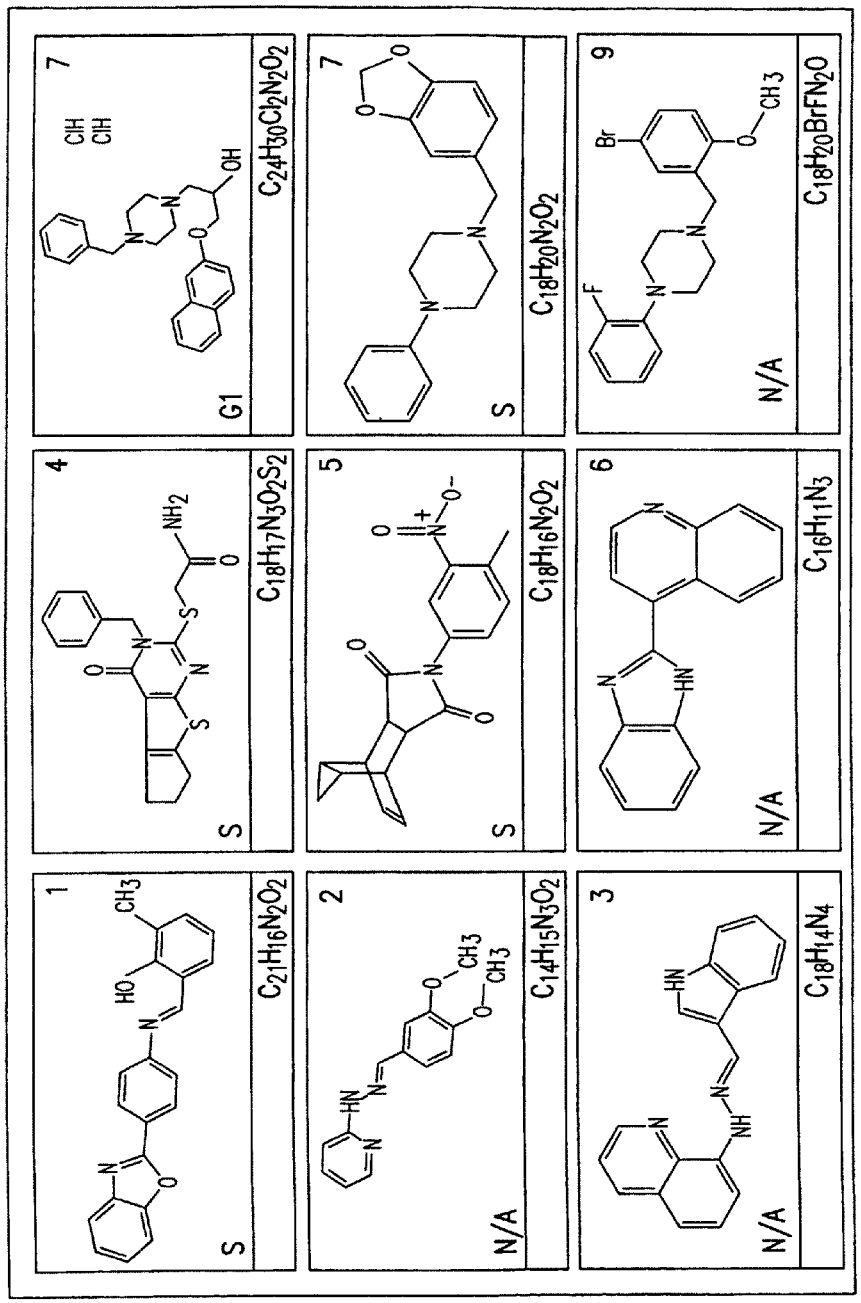
FIG. 1 is a table showing the structures of compounds identified in a screen for T-cell ablative activity. Chemical structure, formula, and molecular weight (MW) of the identified compounds are shown. Compound number is indicated in the top right corner, and is used throughout this disclosure. Effects on phases of cell cycle are indicated in the lower left corner of each panel. "N/A" is no effect on cell cycle detectable (see also FIG. 2).
Figure 2A:
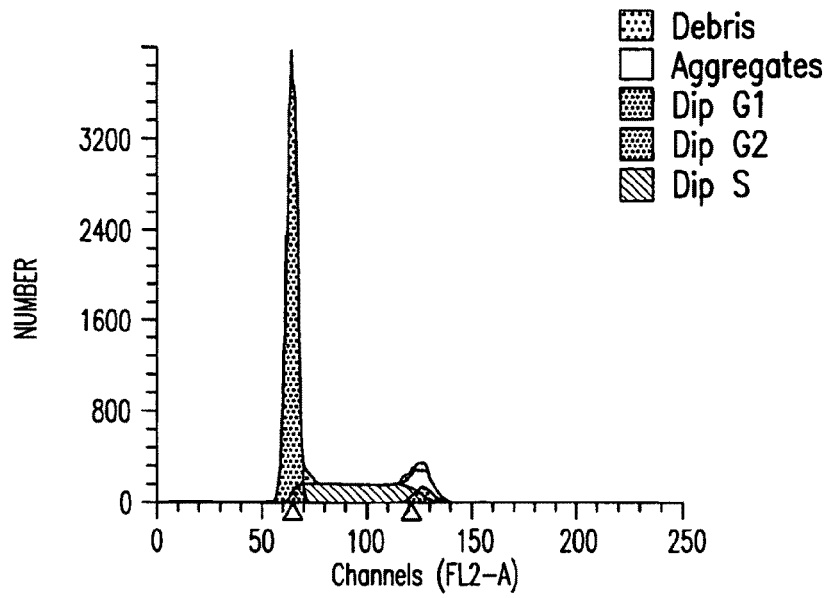
FIG. 2 is a group of cell cycle profiles of active compounds tested in 24 hour zebrafish embryos. Specifically, embryos incubated with E3 fishwater (panel A), hydroxyurea (panel B), compound C4 (panel C), and compound C3 (panel D) are shown. After overnight incubation, single cell solution of embryos was prepared and incubated with propidium iodide. Samples were then subjected to flow cytometry to determine DNA content (X axis). Small arrowheads below the X-axis are placed beneath the diploid (G1) n=2 peak, and the tetraploid (G2/M) n=4 peaks. Cells between these two peaks are in S phase. Cells to the left of the G1 peak (sub G1 peak) have lost chromosomes (n<2), and are presumably dying (indicated as % debris in the right hand legend of each panel). Relative numbers of cells (Y-axis) in the different phases of the cell cycle are given on the right side of each panel. Large arrowheads in panels B and C point to the increased number of cells in S phase (S phase arrest). Note the lack of cell cycle effects and of debris caused by E3 fishwater (panel A) and compound C3 (panel D) compared to hydroxyurea (panel B) and compound C4 (panel C).
Figure 2B:
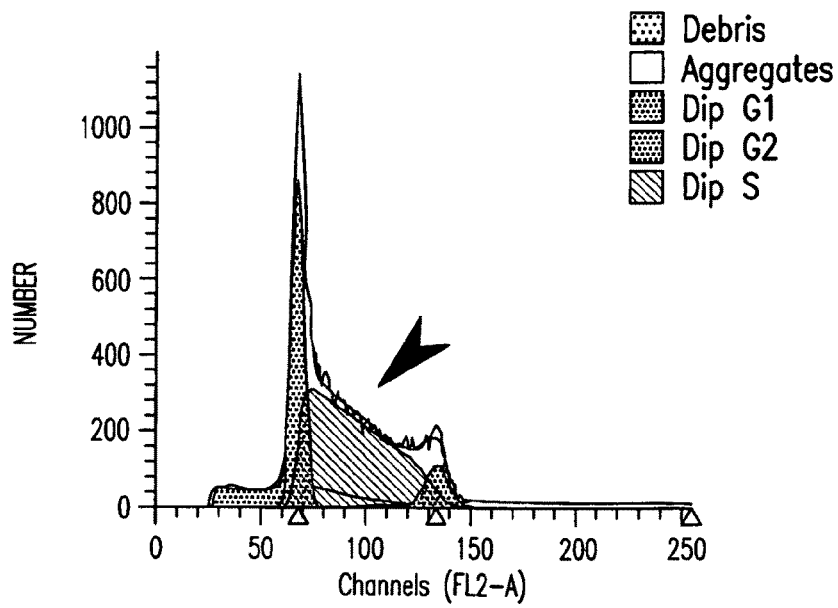
Figure 2C:
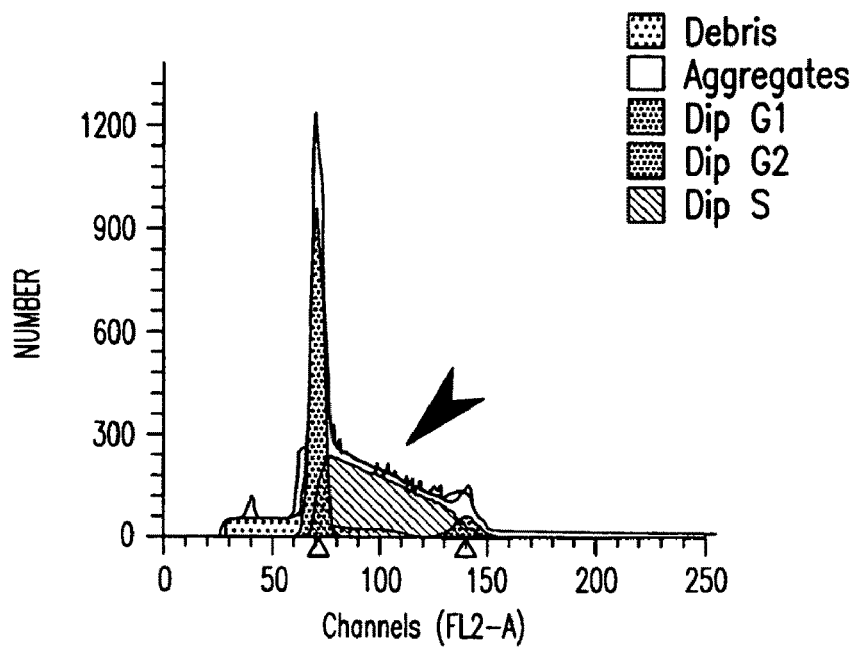
Figure 2D:
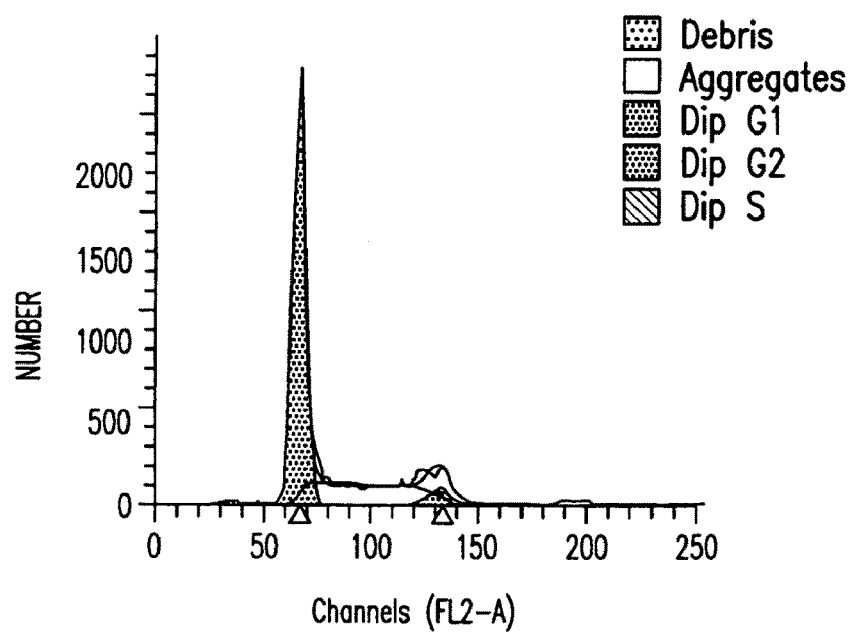

The materials, compounds, compositions, articles, devices, and methods described herein may be understood more readily by reference to the following detailed description of specific aspects of the disclosed subject matter and the Examples included therein and to the Figures.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms that shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the compound" includes mixtures of two or more such compounds, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that these data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

By "pharmaceutically acceptable" is meant a material that is not biologically or otherwise undesirable, i.e., the material can be administered to an individual along with the selected compound without causing any undesirable biological effects or interacting in a deleterious manner with any of the other components of the pharmaceutical composition in which it is contained.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, sulfo-oxo, or thiol, as described herein. A "lower alkyl" group is an alkyl group containing from one to six carbon atoms.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, sulfo-oxo, or thiol as described herein.

The term "alkoxy" as used herein is an alkyl or cycloalkyl group bonded through an ether linkage; that is, an "alkoxy" group can be defined as -$OA^1$ where $A^1$ is alkyl or cycloalkyl as defined above. "Alkoxy" also includes polymers of alkoxy groups as just described; that is, an alkoxy can be a polyether such as -$OA^1$-$OA^2$ or -$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, substituted or unsubstituted alkyl, cycloalkyl, alkoxy, alkenyl, cycloalkenyl, alkynyl, aryl, heteroaryl, aldehyde, amino, carboxylic acid, ester, ether, halide, hydroxy, ketone, azide, nitro, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, sulfo-oxo, or thiol, as described herein.

The term "cycloalkynyl" as used herein is a non-aromatic carbon-based ring composed of at least seven carbon atoms and containing at least one carbon-carbon triple bond. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or substituted or unsubstituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —OC(O)$A^1$ or —C(O)O$A^1$, where $A^1$ can be a substituted or unsubstituted alkyl, cycloalkyl, alkenyl, cycloalkenyl, alkynyl, cycloalkynyl, aryl, or heteroaryl group as described herein.

The term "ether" as used herein is represented by the formula $A^1OA^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein.

The term "halide" as used herein refers to the halogens fluorine, chlorine, bromine, and iodine.

The term "hydroxyl" as used herein is represented by the formula —OH.

The term "ketone" as used herein is represented by the formula $A^1C(O)A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "sulfo-oxo" as used herein is represented by the formulas —S(O)$A^1$, —S(O)$_2A^1$, —OS(O)$_2A^1$, or —OS(O)$_2$O$A^1$, where $A^1$ can be hydrogen or a substituted or unsubstituted alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2A^1$, where $A^1$ can be hydrogen or a substituted or unsubstituted alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group as described herein.

The term "sulfonylamino" or "sulfonamide" as used herein is represented by the formula —S(O)$_2$NH—.

The term "thiol" as used herein is represented by the formula —SH.

"$R^1$," "$R^2$," "$R^n$," "L," "X," "Y," and "Z" as used herein can, independently, possess one or more of the groups listed above. For example, if $R^{1'}$ is an alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an ester," the ester group can be incorporated within the backbone of the alkyl group. Alternatively, the ester group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compositions

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a composition is disclosed and a number of modifications that can be made to a number of components of the composition are discussed, each and every combination and permutation that are possible are specifically contemplated unless specifically indicated to the contrary. Thus, if a class of components or moieties A, B, and C are disclosed as well as a class of components or moieties D, E, and F and an example of a composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Disclosed herein are compounds and analogs thereof that can be used to modulate T-cell growth and/or survival. These compounds were identified from the DIVERSet library (Chembridge, San Diego, Calif.) that have anti-T cell activity. A combination of drug testing in live, transgenic zebrafish and in vitro against human T-ALL cell lines was employed. After testing 26,000 compounds for the desired activity, structurally related "lead" compounds that kill T cells in vivo and in vitro and that have no effect on the cell cycle were identified.

In one aspect, the disclosed pharmaceutical compositions comprising compounds having Formula I or a pharmaceutically acceptable salt thereof.

Ar$^1$-L-Ar$^2$     I wherein Ar$^1$ and Ar$^2$, are independent of one another, a substituted aryl, unsubstituted aryl, substituted heteroaryl, or unsubstituted heteroaryl; and L is a bond or a linker spanning two, three, four, or five atoms, and a pharmaceutically acceptable carrier. The compounds represented by Formula I can be synthesized by methods well know in the art or are commercially available.

The presence of aryl groups (Ar$^1$ and Ar$^2$), and of an unsaturated or aryl liker (L), results in many of the compounds disclosed herein possessing photochemical activity and can serve as photochromic agents, in addition to their immunomodulatory activity. Further, these disclosed compounds can often possess metal chelating activity.

Aryl Groups, Ar$^1$ and Ar$^2$

In Formula I above, the moieties Ar$^1$ and Ar$^2$ are substituted aryl, unsubstituted aryl, substituted heteroaryl, or unsubstituted heteroaryl groups. Some specific examples of aryl groups that are suitable as Ar$^1$ and/or Ar$^2$ are shown in Formulae IIA-C.

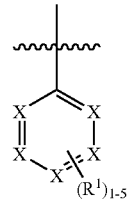
IIA

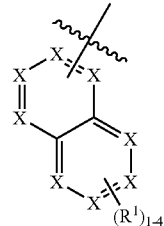
IIB

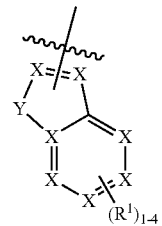
IIC wherein each X is, independent of the others, N, CH, or CR$^1$; Y is CH$_2$, O, or NH; and each R$^1$ is, independent of the others, hydrogen, halide, hydroxy, amino, azide, nitro, amine, thiol, a substituted or unsubstituted alkyl, substituted or unsubstituted alkoxyl, substituted or unsubstituted alkenyl, substituted or unsubstituted alkynyl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, substituted or unsubstituted heterocycloalkynyl, aryl, or heteroaryl, with the proviso that when X is N, it is not substituted with an R$^1$ substituent and with the understanding that the valences of each X and Y are not violated. Pharmaceutically acceptable salt of these moieties are also contemplated.

Some additional examples of aryl groups that are suitable as Ar$^1$ and/or Ar$^2$ are shown in the following table.

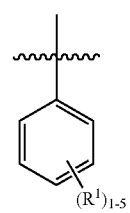 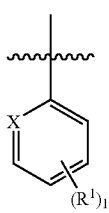 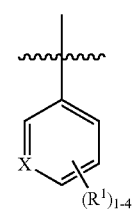

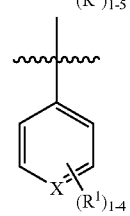 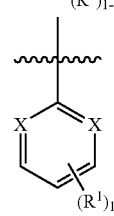 

-continued

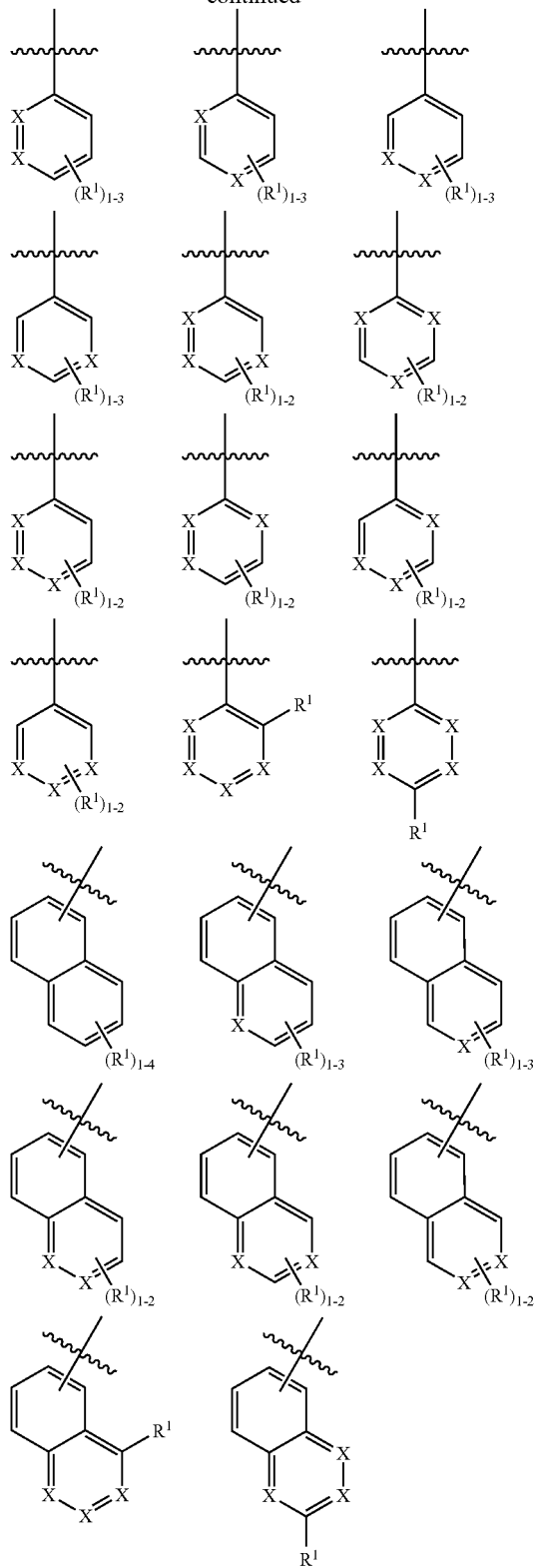

wherein X is N; and each R¹ is as defined before, with the proviso that X is not substituted with an R¹ substituent and with the understanding that the valences of each X are not violated. Pharmaceutically acceptable salt of these moieties are also contemplated.

Some additional examples of aryl groups that are suitable as Ar¹ and/or Ar² are shown in the following table.

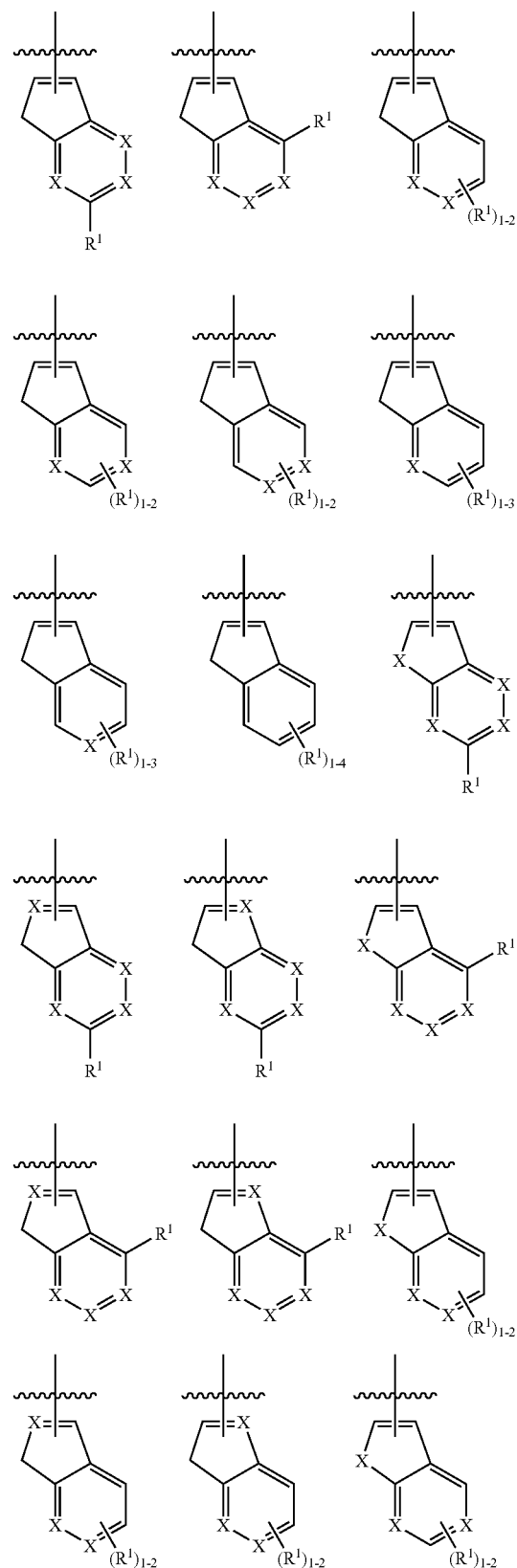

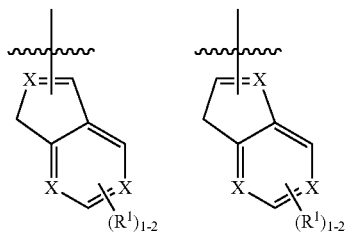
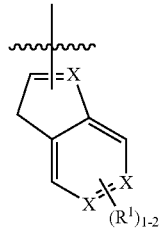
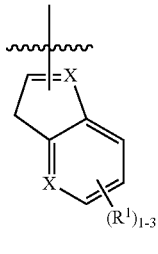
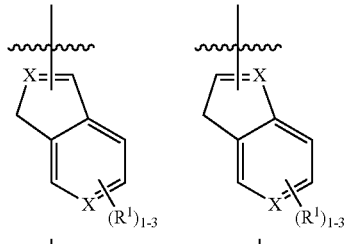
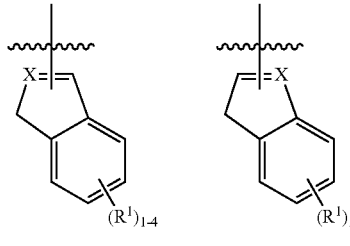

wherein X is N or NH; and R¹ is as defined before, with the proviso that X is not substituted with an R¹ substituent and with the understanding that the valences of each X are not violated. Pharmaceutically acceptable salt of these moieties are also contemplated.

Some specific examples of Ar¹ and/or Ar² groups are:

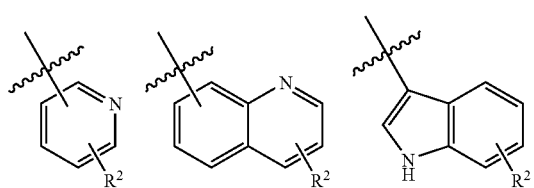

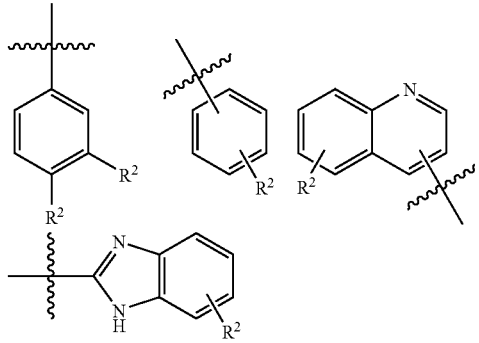

wherein $R^2$ is, independent of the others, H, alkyl, alkoxyl, halide, hydroxyl, or amino. Pharmaceutically acceptable salt of these moieties are also contemplated.

Other specific examples of Ar1 and/or Ar2 groups are unsubstituted phenyl, chloro-phenyl, fluorophenyl, acetyl-phenyl, methoxyphenyl, othro-dimethoxylphenyl, naphtyl, and furanyl.

Linkers

The Linker ("L" in Formula I above) can be a single sigma bond that joins Ar¹ to Ar². Alternatively, the Linker can be a moiety that spans from 1 to 6 atoms. For example, the Linker can span from 2 to 5 atoms, from 3 to 4 atoms, from 1 to 3 atoms, from 4 to 6 atoms, or from 3 to 5 atoms. Some specific examples of Linkers include, but are not limited to, —O— (i.e., an ether), —S—(i.e., a thioether), methylhydrazine, methylhydrazone, methylenepropyl, butyl, pentyl, 1,3 substituted cyclopentyl, 1,3-substituted cyclohexyl, 1,3-substituted cycloheptyl, 1,4-substituted cyclohexyl, 1,4-substituted cycloheptyl, ethyoxyl, propoxyl, butoxyl, methoxymethyl, methoxyethyl, methoxypropyl, ethoxymethyl, ethoxyethyl, propoxymethyl, methylaminomethyl, methylaminoethyl, methylaminopropyl, ethylaminomethyl, ethylaminoethyl, propylaminomethyl, methoxymethoxymethyl, methoxymethoxyethyl, —C(O)OCH₂—, —C(O)OCH₂CH₂—, —C(O)OCH₂CH₂CH₂—, —CH₂C(O)O—, —CH₂C(O)OCH₂—, or —CH₂CH₂C(O)OCH₂—, including pharmaceutically acceptable salt thereof.

In many examples, the Linker can be a liner moiety. Some specific examples of linear linkers are shown in the following table (the bonds from the Linkers in the following example to the Ar¹ and Ar² moieties are omitted for clarity).

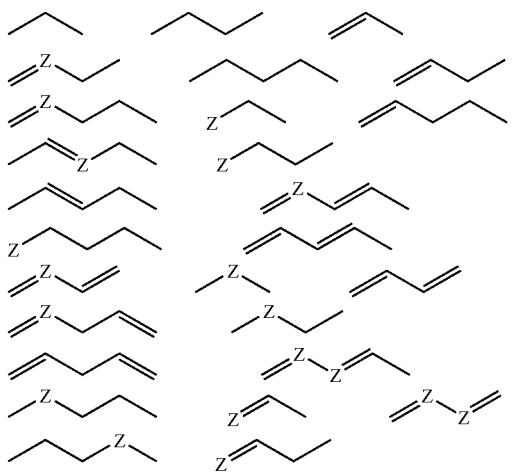

-continued

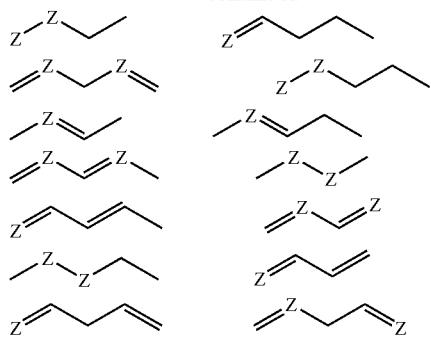

wherein each Z is, independent of the others, O, C(O), S, SO, SO$_2$, N, or NH, and with the understanding that the valences of each Z are not violated in the linker. Pharmaceutically acceptable salt of these moieties are also contemplated.

In other examples, the Linker can be an aryl moiety. Some specific examples of aryl linkers are shown in the following table. The bonds from the Linker to the Ar$^1$ and Ar$^2$ moieties are omitted for clarity but can be in either the ortho, meta, or para configuration.

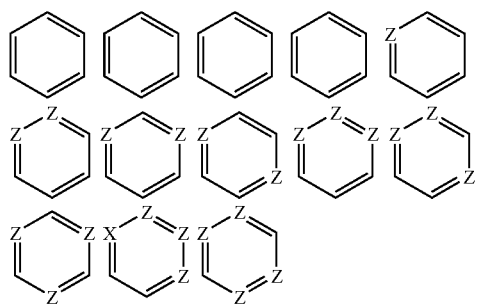

wherein Z is N and with the understanding that the valences of each Z are not violated in the Linker. Pharmaceutically acceptable salt of these moieties are also contemplated.

In other examples, the Linker can be a cyclic moiety. Some specific examples of linear Linkers are shown in the following table. Again, the bonds from the Linker to the Ar$^1$ and Ar$^2$ moieties are omitted for clarity but can be in either the ortho, meta, or para configuration in the case of six membered rings or 1,2-, 1,3-, 1,4-, or 1,5-arrangement in the case of five membered rings.

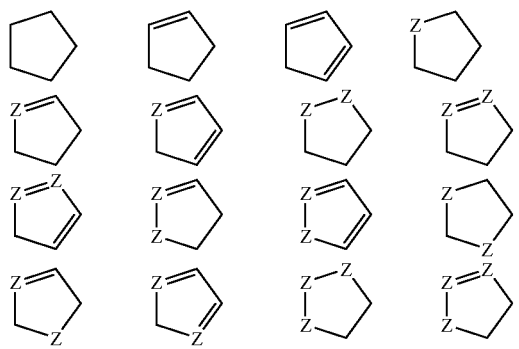

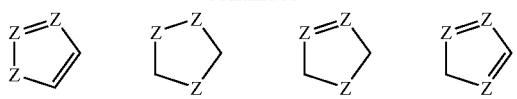
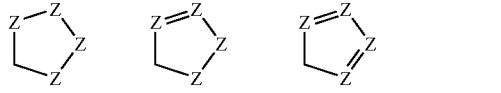
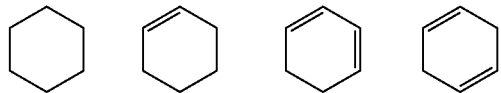
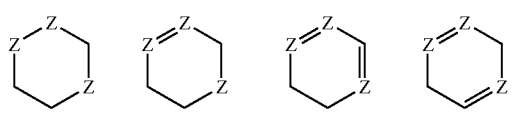
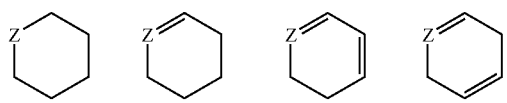
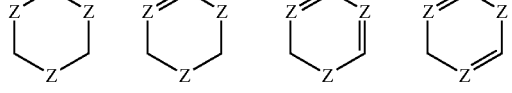
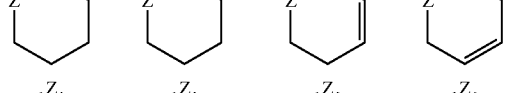
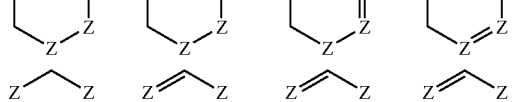
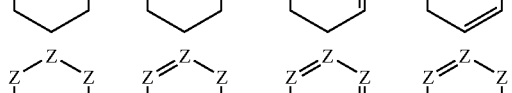
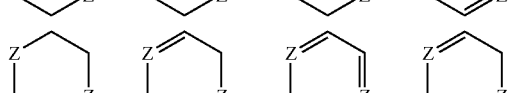
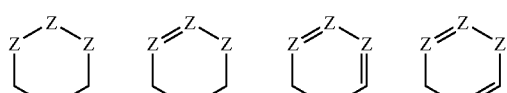
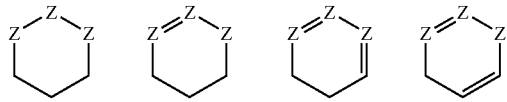

wherein each Z is, independent of the others, O, S, N, or NH, NR$^2$, and with the understanding that the valences of each Z are not violated in the linker and where R$^2$ is a C$_1$-C$_6$ alkyl or C$_1$-C$_6$ acyl, ac. Pharmaceutically acceptable salt of these moieties are also contemplated.

In other examples, the Linker can be —SCH$_2$C(O) NHCH$_2$, —OCH$_2$CH$_2$SO$_2$—, —NHC(O)—, —O—, —S—,

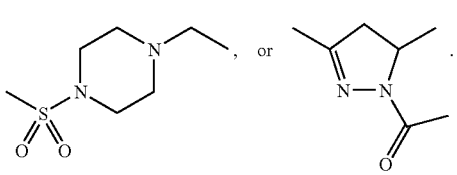

Specific Compounds

Some specific compounds that can be used in the methods disclosed herein are as follows.

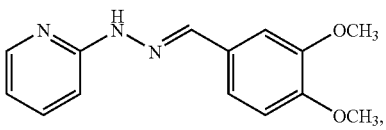

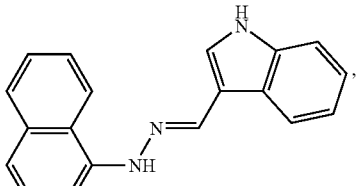

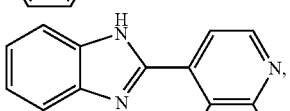

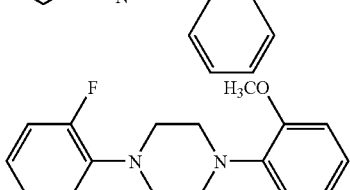

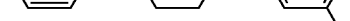

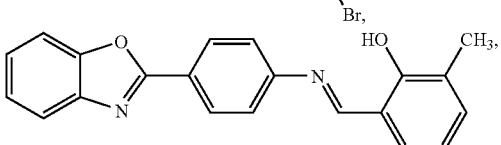

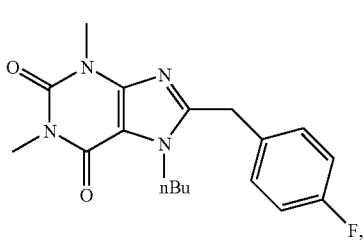

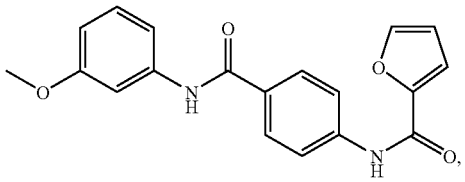

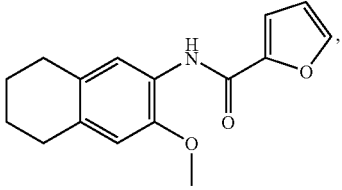

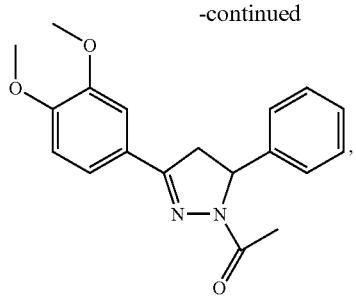

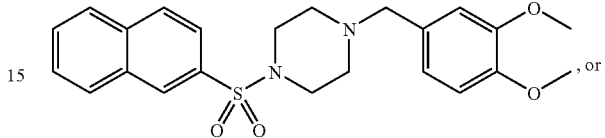

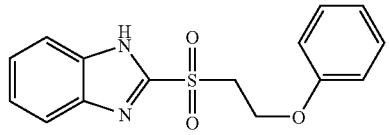

including pharmaceutical acceptable salts thereof.

Still other compounds that have been discovered herein to have activity, though not corresponding to Formula I, are as follows:

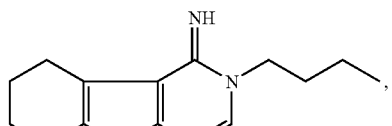

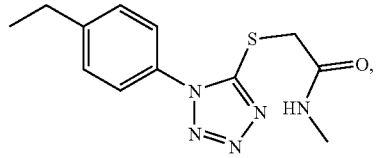

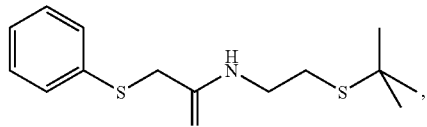

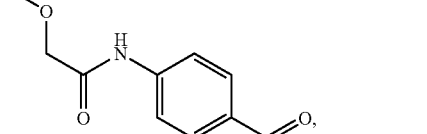

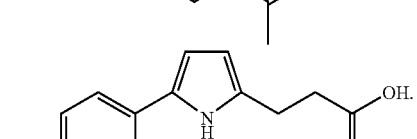

Zebrafish Model of Screening Compounds

Zebrafish present a versatile vertebrate model organism that can be used for human disease modeling (Ackermann and Paw, *Front Biosci* 8:d1227-1253, 2003) and in vivo drug discovery (reviewed in Zon and Peterson, *Nat Rev Drug Discov* 4:35-44, 2005). For example, the heart mutant gridlock, a model for human coarctation of the aorta, has been successfully used in a suppressor screen (Peterson et al., *Nat Biotechnol* 22:595-599, 2004), and identified two novel compounds that are thought to activate the VEGF pathway. Another chemical suppressor screen using the cancer-prone zebrafish cell cycle mutant crash and burn (crb) (Shepard et al., *Proc Natl Acad Sci USA* 102:13194-13199, 2005) identified persynthamide, one out of 16,000 small molecule compounds that suppressed the embryonic phenotype associated with a homozygous crb mutation (Stern et al., *Nat Chem Biol* 1:366-370, 2005). Zebrafish are an excellent model for immunology (reviewed in Trede, *Immunity* 20:367-379, 2004), and can develop T-ALL (Langenau, *Science* 299:887-890, 2003). Here, over-expression of the c-myc proto-oncogene-GFP fusion protein created a model of human T-ALL in which leukemia onset and infiltration can be monitored in real time. These studies have validated the zebrafish as an excellent model for human disease, disease gene discovery, and have also shown promise in screening small molecule compound libraries for clinically useful drugs.

The zebrafish screens used herein allow studies in an intact vertebrate organism, while leaving the cell-extracellular matrix interactions intact. They also allow high throughput screening, which is challenging with higher vertebrates. Further, these screens allow one to distinguish between T cell specific effects from general toxicity, which id difficult to ascertain by in vitro testing. Moreover, the compounds identified by these screens are likely to be orally bioavailable. Also, zebrafish larvae have a liver and can therefore, metabolize and activate compounds, such as prodrugs.

Methods of Use

In many cases of refractory or relapsed T-ALL, there is no effective conventional treatment available. However, the compounds and compositions disclosed herein can have alternative mechanisms of action as compared to conventional chemotherapy. Thus, the disclosed compounds and compositions can be a viable substitute treatment option in such desperate cases. For example, the disclosed compounds and compositions can be used in the "therapeutic window" in the week before conventional chemotherapy is given to patients with newly diagnosed T-ALL or B-ALL.

The disclosed compounds and compositions can also be used for other indications that are mediated by T cells, such as rheumatoid arthritis, multiple sclerosis, and graft-vs-host disease (GvHD).

The disclosed compounds can be used in the form of a pharmaceutical composition. A suitable pharmaceutical composition can comprise any of the disclosed compounds with a pharmaceutically acceptable carrier. The disclosed pharmaceutical formulations can be used therapeutically or prophylactically.

By "pharmaceutically acceptable" is meant a material that is not biologically or otherwise undesirable, i.e., the material can be administered to a subject without causing any undesirable biological effects or interacting in a deleterious manner with any of the other components of the pharmaceutical formulation in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. Suitable carriers and their formulations are described in *Remington: The Science and Practice of Pharmacy*, 21$^{st}$ ed., Lippincott Williams & Wilkins, Philadelphia, Pa., 2005, which is incorporated by reference herein for its teachings of carriers and pharmaceutical formulations. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution can be from about 5 to about 8 (e.g., from about 7 to about 7.5). Further carriers include sustained release preparations such as semipermeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

Pharmaceutical compositions can include additional carriers, as well as thickeners, diluents, buffers, preservatives, surface active agents and the like in addition to the compounds disclosed herein. Pharmaceutical compositions can also include one or more additional active ingredients such as antimicrobial agents, anti-inflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed compounds can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, marine oils, and injectable organic esters such as ethyl oleate. Aqueous carriers include water, alcoholic/aqueous solutions, and emulsions or suspensions, including saline and buffered media. Parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical compositions for oral administration include, but are not limited to, powders or granules, suspensions or solutions in water or non-aqueous media, capsules, sachets, or tablets. Thickeners, flavorings, diluents, emulsifiers, dispersing aids, or binders can be desirable.

Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Disclosed herein are methods of treating a patient with a T cell mediated disease comprising administering to the patient an effective amount of any of the compounds or compositions disclosed herein. When used in the above described methods or other treatments, an "effective amount" of one of the disclosed compositions can be employed in pure form or, where such forms exist, in pharmaceutically acceptable salt form, and with or without a pharmaceutically acceptable excipient, carrier, or other additive.

The specific effective dose level for any particular subject will depend upon a variety of factors including the disorder being treated and the severity of the disorder; the identity and activity of the specific composition employed; the age, body weight, general health, sex and diet of the patient; the time of administration; the route of administration; the rate of excretion of the specific composition employed; the duration of the treatment; drugs used in combination or coincidental with the specific composition employed and like factors well known in the medical arts. For example, it is well within the skill of the art to start doses of a composition at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose.

The dosage can be adjusted by the individual physician or the subject in the event of any counterindications. Dosage can vary, and can be administered in one or more dose administrations daily, for one or several days. Guidance can be found in the literature for appropriate dosages for given classes of pharmaceutical products.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in C or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Experiments described in this document are carried out in zebrafish embryos (cell cycle experiments) and lck-GFP transgenic larvae (5 to 8 days after fertilization), and in human cell lines (Jurkat is a human T cell leukemia, RS4; 11 is a human B cell leukemia and HEK293 is a human kidney cell line).

Example 1

The In Vivo Assay

A phenotype-drive screen was conducted to identify mutants of T cell and/or thymus development. In this screen 6 complementation groups of T cell deficient mutants with various degrees of thymus abnormalities were identified. These mutants were characterized in detail, and two of the mutants were positionally cloned. The first, earl grey (egy) is now in press at PNAS (Trede et al., *Proc Natl Acad Sci USA*, in press, 2007). The egy mutant has a defect in splice factor recycling, which leads to tissue-specific defects, including thymus development. The second mutant, ceylon (cey), has a defect in the transcription factor Sox9b that leads to abnormal T cell development in a thymus anlage that is more voluminous than its wild-type counterpart.

To extend the versatility of the system, a transgenic line of zebrafish was generated; in this line all T cells are tagged with green fluorescent protein (GFP). GFP is driven by the T cell specific p56$^{lck}$ promoter (Langenau et al., *Proc Natl Acad Sci USA* 101:7369-7374, 2004). Using this transgenic line (lck::eGFP), T cell biologic processes such as homing and engraftment of transplanted cells in living zebrafish was demonstrated. In addition, T cells were shown to be sensitive to ionizing radiation and were ablated by treatment with dexamethasone (Langenau et al., *Proc Natl Acad Sci USA* 101:7369-7374, 2004).

The lck::eGFP transgenic line was used to conduct a new phenotype-driven screen, where mutants with T cell deficiency (absence of GFP signal in thymus) and lymphoproliferation/leukemia/lymphoma are easily uncovered by in vivo fluorescent imaging. This screen yielded one confirmed immunodeficient mutant, and this mutation was mapped to chromosome 8. In addition, three separate dominant leukemic mutants were identified.

Example 2

Compound Screening

Figure 4A:
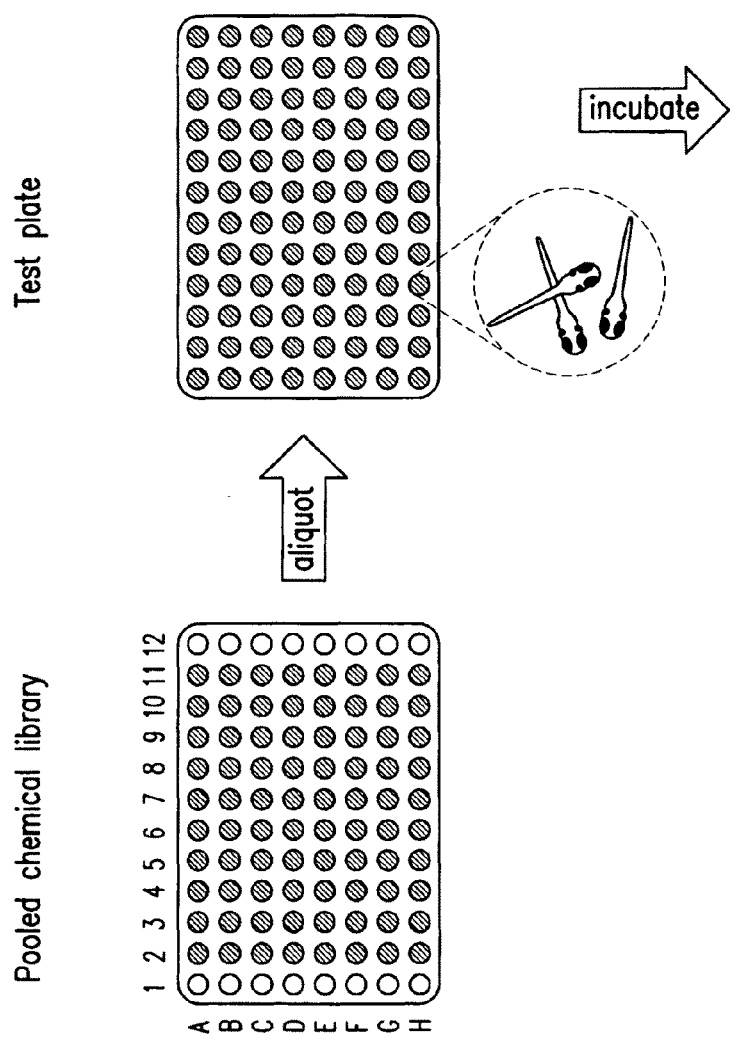
FIG. 4 is a schematic of the experimental set-up of drug screen using DIVERSet small molecule library and lck-GFP transgenic zebrafish. Beginning at the top of the figure, three day 6 pf transgenic larvae are arrayed in 300 µL of E3 embryos water into each of the 96 wells of a round bottom tissue culture plate (except G1, H1, G12, H12). Controls are added in triplicate: DMSO (A1-C1), E3 (D1-F1), dexamethasone 25 µM (A12-C12), and methanol (D12-F12). Then, five compounds from the DIVERSet library are added to each well at a final concentration of 5 µM. Plates are incubated at 280° C. for 48 hours, and are inspected by fluorescence microscopy at 24 and 48 hours. At the bottom of the figure, representative examples of larvae incubated in controls, inactive and active compounds, are shown (right side). Compounds from wells identified as active are tested individually in triplicates. One of the five compounds that is active in all three wells is identified and is worked up further (left side).
Figure 4B:
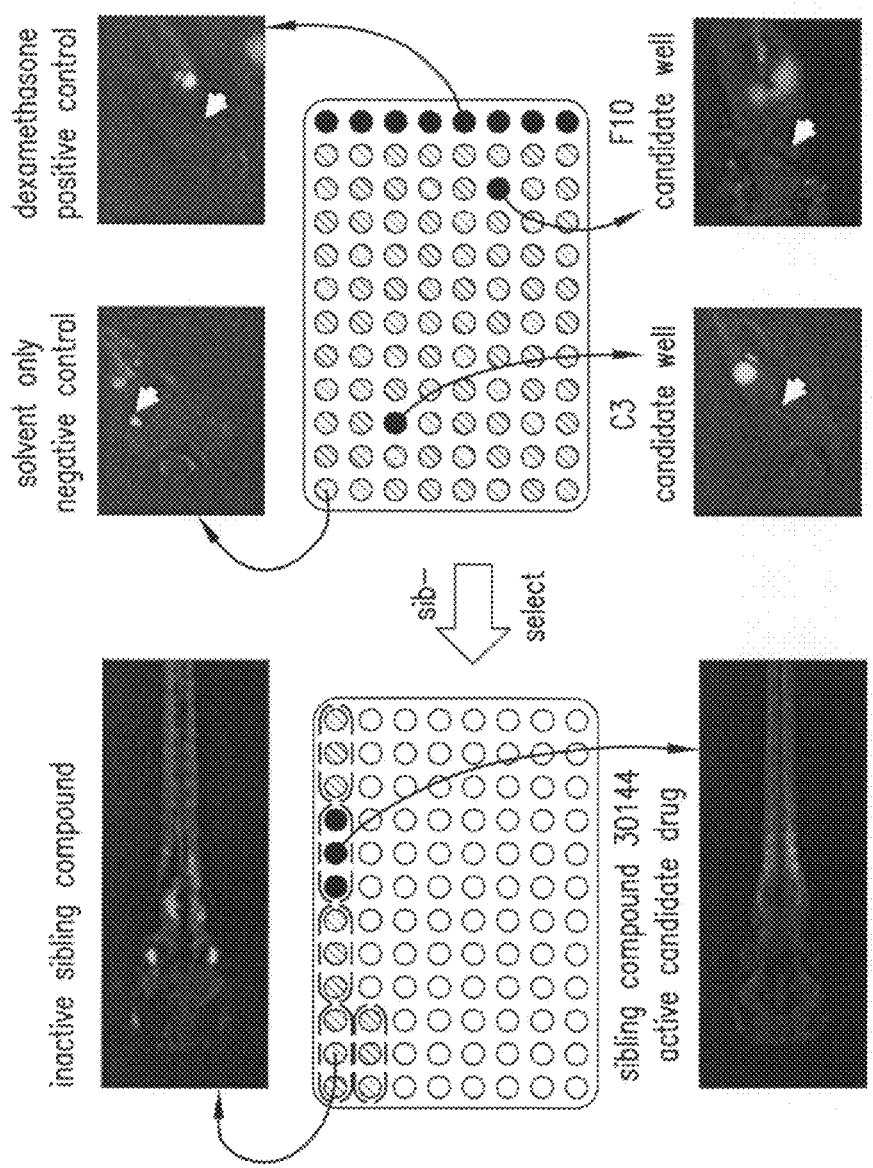

Based on the above observation that zebrafish T cells can be killed by the small molecule dexamethasone (MW 392) (Langenau et al., *Proc Natl Acad Sci USA* 101:7369-7374, 2004) a screen for novel compounds with a similar T cell ablative profile was performed. Specifically, efficacy of the small molecules from the DIVERSet library (Chembridge, San Diego, Calif.) towards eliminating T cells from the thymus of day 6 post fertilization (dpf) lck::eGFP transgenic zebrafish was conducted (FIG. 4). This library is a diverse, pre-designed collection of 50,000 drug-like small molecules that were selected based on 3D steric and electronic features to cover the broadest part of biologically relevant pharmacophore diversity space.

26,000 molecules in the library were tested and nine were identified that ablated T cells dramatically or completely. Structure, chemical composition, and molecular weight (MW) of identified compounds are indicated in FIG. 1. Compound number is indicated in the top right corner of FIG. 1. Effects on phases of cell cycle are indicated in the lower left corner of each panel. N/A is no effect on cell cycle detectable.

Cell Cycle Profiles

All of these compounds were tested for effects on the cell cycle in zebrafish embryos. Zebrafish embryos were incubated at 4 hours post fertilization with compounds or controls. After overnight incubation in compounds, single cell solution of embryos was prepared and incubated with propidium iodide. Samples were then subjected to flow cytometry to determine DNA content. Five compounds caused various degrees of cell cycle arrest, predominantly in S phase. Compounds 2, 3, 6, and 9 did not have any appreciable effect on the cell cycle. Examples are depicted in FIG. 2.

In FIG. 2, embryos incubated with (A) E3 fishwater, (B) hydroxyurea, (C) compound C4, and (D) C3 are shown. Diploid (G1, n=2) and tetraploid (G2/M, n=4) peaks are identified on the X-axis. Small arrowheads below the X-axis are placed beneath the dipoid (G1) n=2 peak, and the tetraploid (G2/M) n=4 peaks. Cells between these two peaks are in S phase. Cells to the left of the G1 peak (sub G1 peak) have lost chromosomes (n<2) and are presumably dying (indicated as % debris in the right hand legend of each panel). Relative numbers of cells (Y axis) in the different phases of the cell cycle are given on the right side of each panel. Large arrowhead in panels B and C point to the increased number of cells in S phase (S phase arrest). Note the lack of cell cycle effects and of debris caused by E3 fishwater (panel A) and C3 (panel D) compared to hydroxyurea and compound C4.

Cell culture experiments: Cells were incubated at 37° C. in 75 mL flasks in RPMI containing 10% FBS, 5 mL Penicillin/Streptomycin (100×) in a total volume of 20 mL. Cells were counted using a hemocytometer, and 25,000 cells were plated in each well of a 96-well plate. Compounds and controls were added and cells were harvested after a 48 hr incubation period.

To assess effects of compounds, cell viability was measured. For this, cells were incubated with MTT [3-(4,5-dimethyldiazol-2-yl)-2,5 diphenyl Tetrazolium Bromid], a compound that is transformed into a formazan crystal by mitochondrial dehydrogenases. After crystal solubilization with DMSO a blue color (that is proportional to the amount of crystal formed) can be measured. Formazan solution absorbs light at 550-570 nm but not at 620-650 nm. 620-650 nm absorbency results from cell debris and well imperfections. Final optical density (OD) obtained from formazan formation was calculated OD=L1-L2 (background).

In Vitro Assays

Figure 3:
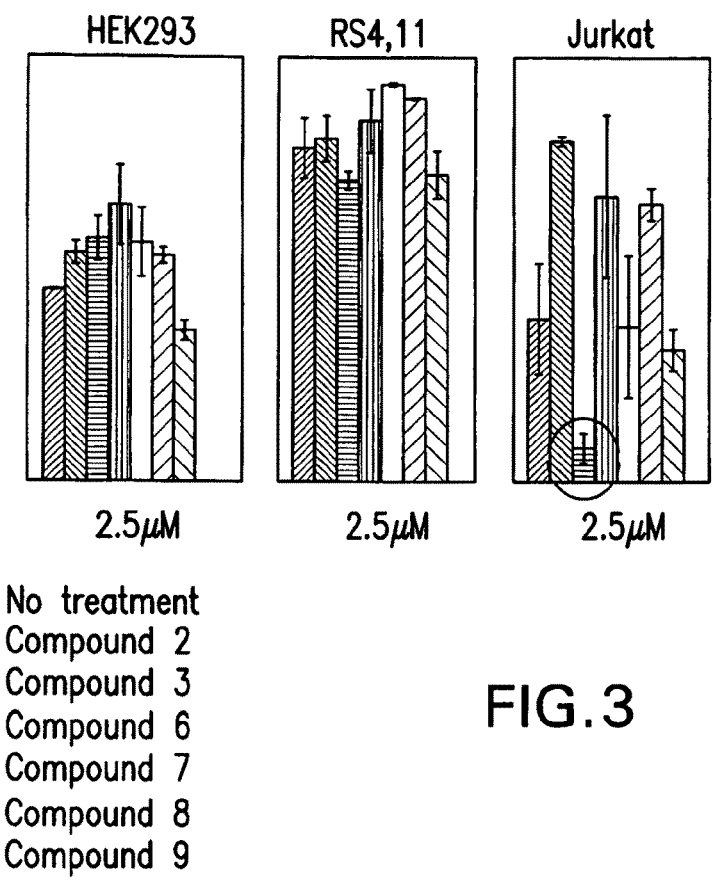
FIG. 3 is a graph showing viability of human T-ALL lines incubated with individual compounds. Specifically, two human ALL lines (B-ALL: RS4; 11 and T-ALL: Jurkat) were incubated on day 0 with serum or with 2.5 µM of the indicated compounds (except for aphidicolin 1 µM and cyclosporine 1.5 µM). 48 hours later, cells were tested for viability by MTT test. Results from the mean of 3 to 4 experiments carried out in triplicate (individual dots) and the mean of all experiments (horizontal bar) are indicated. Results are shown for compounds without a cell cycle effect (B). Viability of untreated cells was arbitrarily set at 1.0.

Next, the nine compounds were tested for activity against the human T-ALL line: Jurkat and the human B-ALL line RS 4; 11. The latter was transduced with the luciferase gene for ease of detection in xenograft models. As shown in FIG. 3, the T cell leukemia line and zebrafish T cells responded similarly to compound 3. However, neither the kidney cell line, nor the B-ALL were affected by compound 3, pointing to a specific effect of compound 3 on T-cells.

Taken together, 20 out of 38,000 DIVERSet compounds were identified that have anti-T cell activity in zebrafish larvae. To date nine were further tested and one compound (compound 3) was identified that kills the human T-ALL line Jurkat in vitro at an effective concentration of 2.5 µM, and does not affect the cell cycle.

Example 3

Structural Homologues

Structurally related compounds to compounds C2, C3, C6, and C9 in FIG. 1 can be searched for in a manner similar to that disclosed above for identifying the compounds C2, C3, C6, and C9. For example, the simplest compound, C6, is less active in vivo than compounds C2 and C3 (23 µM vs 3 µM). While not wishing to be bound by theory, this may be due to decreased bioavailability (uptake, metabolism) or decreased affinity to a target molecule. The main distinction between compounds C6 and C3 is the presence of a hydrazone-like linker in C3. This structure is also found in the more active C2 and can therefore be maintained in a structural homology search.

In a structure-function search, dispensable as well as important moieties can be identified. In addition, active compounds with functional groups such as amides or hydroxyl groups that can subsequently be used for target identification can be identified. One can use the entire Chembridge database, comprising 1,000,000 compounds. A search algorithm can be used to look for related compounds with n % similarity to compounds C2, C3, C6, and C9. In addition, Web-based searches (e.g., the Sigma database, emolecules, and CHEMSEARCH) can be used.

Because three structurally related compounds are available with similar characteristics in terms of their effects on the cell cycle and on T cell survival. Therefore, functionally important moieties are identifiable and a database search can lead to related molecules with the desired activity.

Example 4

Compound Screenings

Structurally related compounds identified as described in Example 3, can then be subjected to iterative cycles of testing in live zebrafish (see FIG. 4 bottom), followed by cell cycle analysis, to ascertain absence of delay or blocks of cell cycle phases. Effects of small molecule drugs on the cell cycle can be determined straightforwardly in zebrafish embryos (Stem et al., *Nat Chem Biol* 1:366-370, 2005; Murphey et al., *Chem Biol Drug Des* 68:213-219, 2006).

Example 5

Solubility Studies and Pharmacokinetic Studies

Solubility studies of compounds can be performed by HPLC. Further, a pharmacokinetic protocol can be established to permit reliable measurement of the compounds. Compounds 2, 3, and 6 have a favorable isoquinoline ring structure, so that determination of serum concentration can be done by fluorescence emission measurement. Compounds can either be injected or given orally and blood samples can be obtained at 10 different time points (starting at 2 minutes to 24 hours) on 30 mice (triplicate) and can subsequently be analyzed. As some compounds may have such unfavorable PK characteristics as to be unusable, PK studies can first be done on a non-GLP basis. This allows compounds to be retested after modification without prohibitive expense. Once a compound has passed all preliminary tests and is shown to be efficacious, PK studies can be redone under GLP conditions.

Next, LC50 and maximum tolerated dose (MTD) can be determined. Histologic slides from 9 organs (3 sections per slide) can be prepared and analyzed by a mouse pathologist. Dose-limiting toxicity can also be evaluated histologically, by blood counts and body weight.

While neither bioavailability nor toxicity can be accurately predicted, the fact that the compounds were non-toxic and active in a living vertebrate by simply adding the compound to water increases the likelihood of a favorable drug profile.

Example 6

Assessing In Vivo Efficacy

Once MTD is established and the toxicology profile of a given compound is favorable, efficacy testing can be carried out. The goal is to test if engraftment of a human T-ALL line in immunocompromised mice can be prevented or reversed by treatment with an active compound. A human T-ALL Jurkat has been transduced with the luciferase reporter gene (Jurkat Luc Neo, LN). This allows accurate monitoring of engraftment and expansion in living mice using a CCD camera. Reduction in tumor burden at any time point can be accurately measured by injecting the luciferase substrate luciferin, followed by determining the area under the curve of light emission for each mouse. The endpoint is a change in emission in treated compared to the untreated group of animals. The efficacy of this system has been demonstrated in previous experiments (Walensky et al., *Science* 305:1466-1470, 2004).

For each experiment, ten nude mice can be injected with $10^6$ Jurkat LN cells on day 0. Five animals can receive compound, the other five can receive saline. Animals can be injected with luciferin once a week, and light emission can be measured with a CCD camera. Previous studies (Walensky et al., *Science* 305:1466-1470, 2004) indicate that significant differences between the treatment groups can be observed at one to four weeks of compound administration. For power calculations, each treatment group can be compared to control at a fixed time point (e.g., 4 weeks after injection of Jurkat LN cells) using a t-test with a two-sided alpha=0.05 significance level, and that the response is log-normally distributed with coefficient of variation equal to 0.25 in each group. Under these assumptions 15 mice per group will provide 86% power to detect a 25% reduction in the treatment group compared to control. This means that three sets of experiments will yield the answer as to whether or not the compound is efficient in killing human T-ALL cells.

When compound half-life is sufficiently long and/or compound solubility is limiting (so that large volumes have to be given), daily or twice daily intraperitoneal administration can be performed. When a compound has a short half-life, Alzet osmotic pumps can be implanted into the skin of nude mice on the day of Jurkat LN injection. Alzet pumps come in three different sizes and in mice can deliver up to 6 μL per day for up to 4 weeks by continuous infusion. The feasibility of this approach was recently demonstrated for the somatostatin-activating molecule TT-232 in treating AML cells injected into nude mice (Tejeda et al., *Anticancer Res* 25:325-330, 2005). If one assumes an average compound MW of 300, an average mouse weight of 20 g, and a treatment dose of 1 mg/kg/d, the required compound concentration will be 10 mM. Most compounds can be formulated at this concentration.

Example 7

Assessing Mechanism of Action

There are three principal characteristics of a successful drug. First and foremost, lack of toxicity is of pivotal importance. Next, activity of a new compound against a target is a self-evident prerequisite for successful drug development. Finally, knowledge of the precise molecules targeted by the drug is desirable. While this is not an absolute requirement (targets for many of the drugs in current use have not been established), identification of the molecular target/pathway through which a drug exerts its effect is advantageous for several reasons: 1) Side effect profiles are more readily predictable. 2) Possible positive or negative interactions with other concomitantly used drugs may be anticipated. 3) Molecular consequences of drug administration such as for example enzyme inhibition can be directly assayed. 4) Knowledge of the target allows supplementary rational drug design. To analyze the pathway altered and the molecule(s) targeted by the disclosed compound, the following experiments can be performed.

Pathway Analysis

Figure 5:
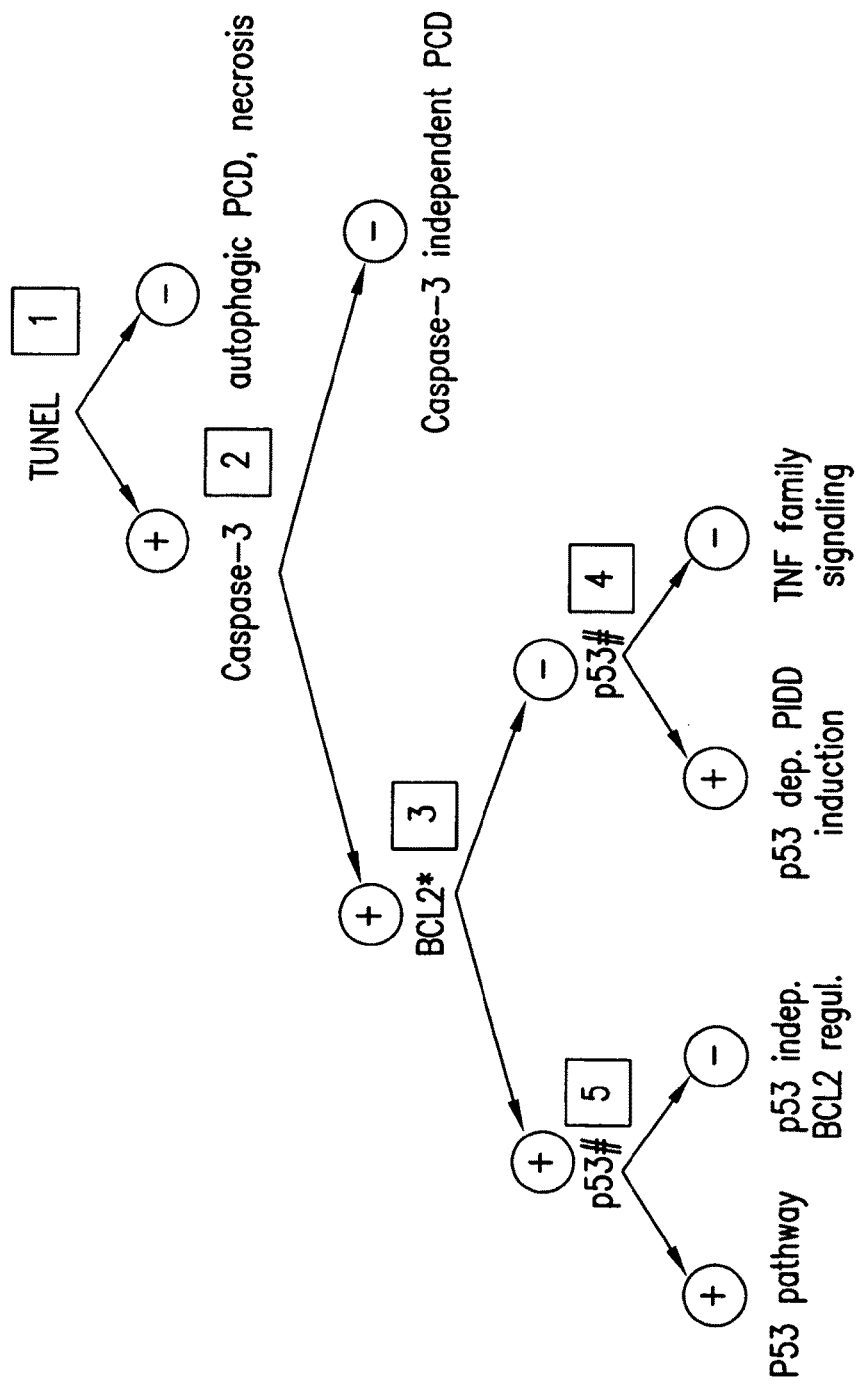
FIG. 5 is a schematic of a decision tree for workup of pathway altered by a compound. "PCD" is programmed cell death; "PIDD" is p53 induced protein with death domain; "*" is T cells from Rag2::BCL2-eGFP transgenic line that are killed (−) or survive (+); "#" is T cells from p53 mutant J19 line containing the lck-GFP transgene that are killed (−) or survive (+). Individual steps in the workup are indicated by the numbered boxes.

The vast majority of anti-cancer drugs lead to programmed cell death (PCD) by apoptosis (Tolomeo and Simoni, *Curr Med Chem Anticancer Agents* 2:387-401, 2002). In order to determine if activity of the disclosed compound is effected through apoptosis, TUNEL staining can be performed (FIG. 5, step 1). This can reveal the level of apoptosis in T cells residing in the larval thymus of treated relative to untreated individuals. If no increase in TUNEL positive cells is found, autophagic PCD or necrosis are the likely cause of cell death (Jaattela and Tschopp, *Nat Immunol* 4:416-423, 2003; Gozuacik and Kimchi, *Curr Top Dev Biol* 78:217-245, 2007). This scenario could occur if for example there was compound-mediated activation of RIP kinase pathway (Holler et al., *Nat Immunol* 1:489-495, 2000). If increased TUNEL stain is documented in compound-treated cells, drug-treated larvae can be stained with anti-caspase-3 antibody (step 2). If no increase in caspase-3 activity is identified, an independent pathway is deregulated that leads to DNA fragmentation, as in activation induced cell death in T cells (Chhabra et al., *Eur J Jmmunol* 36:3167-3174, 2006).

With increased caspase-3 activity, the next question concerns the involvement of BCL2. There are two main pathways: BCL2-inhibitable and BCL2-independent caspase-3 induction. To test whether the compound-induced T cell death is BCL2-inhibitable, a line of fish from the laboratory of Dr. T. Look (DFCI, Boston, Mass.) where the Rag-2 promoter drives both eGFP and BCL-2 expression can be used (step 3). The functionality of the anti-apoptotic construct was demonstrated by XRT-resistant T cell survival (Langenau et al., *Blood* 105:3278-3285, 2005).

If T cells are not protected by BCL2 overexpression (step 3,-), one can test whether the compound-altered pathway requires intact p53 (step 4). Survival of T cells in the presence of the compound in the p53 inactivated mutant J19 line of zebrafish can be tested. The lck::eGFP transgene has been crossed onto the J19 background to facilitate the readout of compound activity. If T cells die despite the absence of functional p53, the most likely pathway perturbed by the compound is mediated by TNF family signaling (Newton et al., *Curr Biol* 11:273-276, 2001; O'Connor et al., *Cancer Res* 60:1217-1220, 2000), that can be independent of p53 and cannot be inhibited by BCL2 overexpression (step 4,-).

If T cells survive in the absence of p53, a possible explanation would be compound-mediated activation of the PIDD pathway (step 4,+) (Lin et al., *Nat Genet.* 26:122-127, 2000; Berube et al., *Proc Natl Acad Sci USA* 102:14314-14320, 2005). BCL2-inhibitable PCD is triggered by the intrinsic pathway, where a stress signal activates p53. This is followed by p53-mediated activation of pro-apoptotic molecules, such as PUMA, BAX and BAK (Chipuk and Green, *Cancer Cell* 1:289-298, 2006). This p53-mediated apoptotic pathway can be inhibited by BCL2 overexpression (Schmitt et al., *Cancer Cell* 1:289-298, 2002).

If this pathway is altered by the compounds, rescue of T cell apoptosis in the J19 line is expected (step 5,+). However, there is also p53-independent regulation of BCL2 family proteins (Strasser et al., *Cell* 79:329-339, 1994; Esteve et al., *Oncogene* 17:1855-1869, 1998). Here, DNA damage or Rho-mediated ceramide production induce apoptosis in a p53-independent fashion that can be inhibited by BCL2 (Step 5,-).

As all the above pathways can be activated in most cell types, a question concerns the T cell specificity of compound action. One possible explanation is that a cellular protein that is either selectively expressed in T cells, or whose intact function is vital specifically for T cell is the target of the compound. For example, naïve T cells depend on tyrosine kinases, such as p56lck and p59fyn for survival (Seddon and Zamoyska, *J Immunol* 169:2997-3005, 2002). Inhibition of these kinases could lead to PCD induction in T cells by one of the above pathways. Another possibility is that immature T cells and T-ALL lines are more sensitive to the action of the compound. To decide between these possibilities, one can test differential sensitivity of T cells at different stages of development to compound in the OP9-DL cell culture system (Wang et al., *Ann N Y Acad Sci* 1044:210-219, 2005; Wang et al., *Exp Hematol* 34:1730-1740, 2006).

Target Identification

Figure 6:
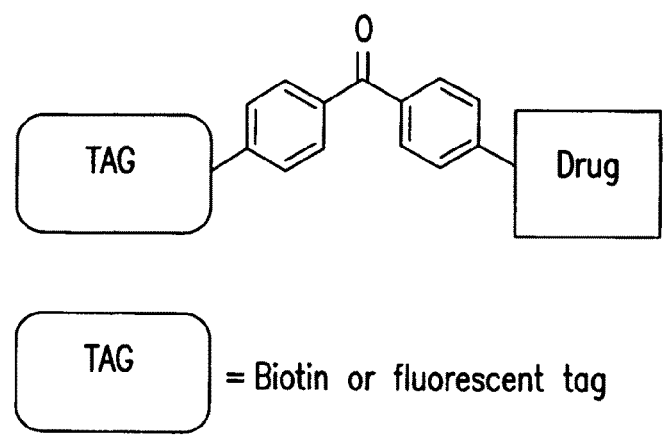
FIG. 6 is a structure of drug tagged with bifunctional group.
Figure 8A:
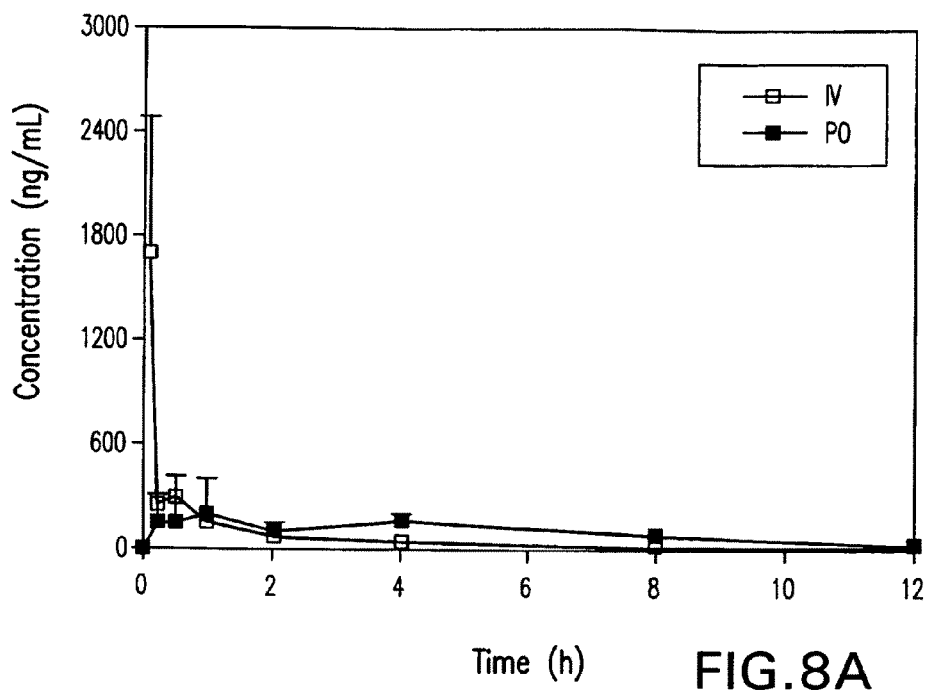
Figure 8B:
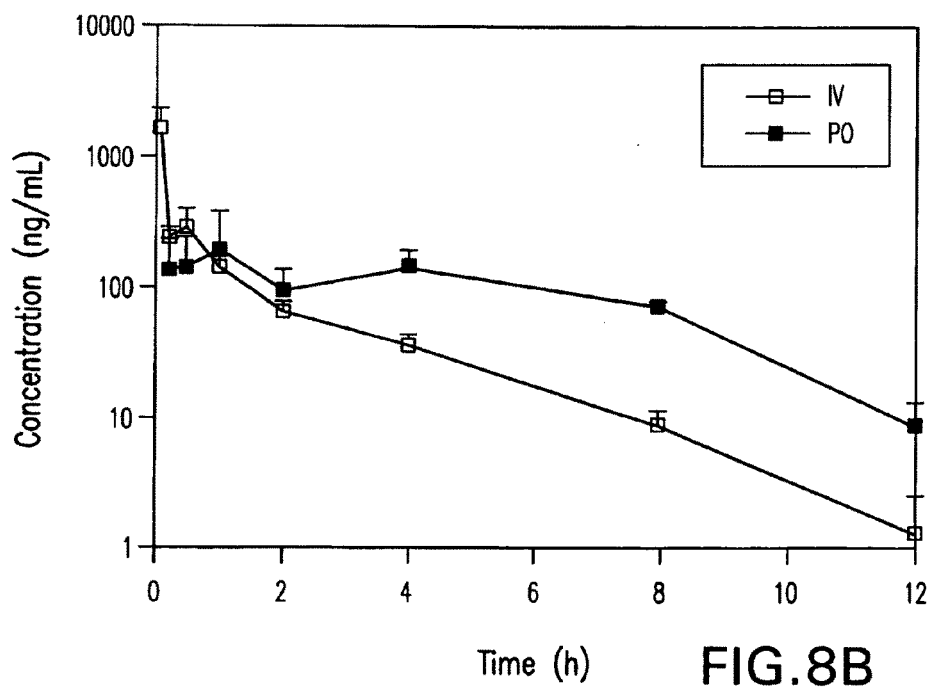

Photoaffinity labeling can be done by identifying an active compound that carries an amide or hydroxyl group to which the photoactive moiety can be coupled. Photo-affinity labeling strategies (PAL) (Hatanaka and Sadakane, *Curr Top Med Chem* 2:271-288, 2002; Spring, *Chem Soc Rev* 34:472-482, 2005). There are various PAL labels reported in the literature. In one example, a bifunctional probe containing a benzophenone moiety and either a biotin or fluorescent tag can be used (FIG. 6) (Wahlstrom et al., *J Biol Chem* 278:5123-5131, 2003). These labels have been well established in terms of synthetic preparation and biological pull down assays. Both whole cell assays and cell lysates can be used. After treatment of cells with labeled compounds and subsequent alkylation by UV activation of the PAL group, one can then pull down protein target(s) of interest with avidin beads. Once isolated, western blot analysis using specific primary antibodies for biotin can be used. Protein bands that are visualized using chemiluminesence can then be excised and subjected to mass spectroscopy analysis to obtain information on molecular weight as well as amino acid sequence of the drug target.

Example 8

Pharmacokinetics of C3

The pharmacokinetics of 1H-indole-3-carbaldehyde quinolin-8-ylhydrazone (Compound C3) was evaluated following intravenous (3 mg/kg) and oral (15 mg/kg) solution administration of 1H-indole-3-carbaldehyde quinolin-8-yl-hydrazone in male Swiss Albino mouse. The effect of the Test Item, 1H-indole-3-carbaldehyde quinolin-8-ylhydrazone on complete blood count (CBC) was also evaluated. Pharmacokinetic phase consisted of two groups, Group 1 and Group 2. Animals in Group 1 were given intravenous bolus dose in a vehicle containing 5% N,N-dimethylacetamide, 5% CREMOPHOR™ EL and 90% Dextrose solution (5% w/v) and those in Group 2 were given oral solution dose in a vehicle, the composition of which was same as that of intravenous formulation. In addition, the effect of Test Item on complete blood count was evaluated following intravenous and oral dose administration along with its vehicle controls. A total of four groups were used each with 6 mice.

From the pharmacokinetic group, predose samples were collected from 3 animals in each group. Following dose administration terminal blood samples were collected at each of the following time points (in triplicate): 0.083 (only for intravenous), 0.25, 0.5, 1, 2, 4, 8, 12 and 24 hours. At each time point, approximately 500 µL of whole blood was withdrawn from the retro orbital sinus and collected in labeled tubes containing dipotassium EDTA as anticoagulant (20 µL of 200 mM K2 EDTA solution per mL of blood). Plasma was separated by centrifuging the whole blood at about 2500 g for 10 minutes at 4° C. within 1 h of sample collection. Separated plasma was stored below minus 50° C. until bioanalysis. A sensitive LC-MS/MS method was used for the quantitation of 1H-indole-3-carbaldehyde quinolin-8-ylhydrazone. The lower limit of quantitation was 1.04 ng/mL. For CBC evaluation, approximately 500 µL of blood was collected in labeled tubes containing dipotassium EDTA as anticoagulant (10 IU/mL of blood) after 48 h of dose administration from all animals.

Plasma concentrations were quantifiable till 12 hours following both intravenous and oral administration. Following intravenous administration, 1H-indole-3-carbaldehyde quinolin-8-ylhydrazone showed moderate clearance (54.78 mL/min/kg; about 60% of liver blood flow) and has a large volume of distribution (4.28 L/kg; about 6 times of total body water). The half-life is approximately 1.7 hours following intravenous administration. Following oral solution dosing, maximum concentration of 1H-indole-3-carbaldehyde quinolin-8-ylhydrazone was reached at 1.0 hour post-dose, indicating fast absorption. The absolute oral solution bioavailability of 1H-indole3-carbaldehyde quinolin-8-ylhydrazone in male Swiss Albino mouse was approximately 26%.

There was no effect on the hematological parameters except for lower white blood cell count in the Test Item treated group following intravenous administration, and lower platelet count in the Test Item treated group following oral administration when compared to corresponding vehicle control group.

Healthy CD-1 male mice were also gavage-fed with compound 3 at concentrations of 50 mg/kg, 15 mg/kg and 5 mg/kg twice per day. No adverse effects were observed over the period of administration (14 days). Hematological, biochemical, immunological and pathological specimen are currently being evaluated.

Materials and Methods

A total of 57 mice were divided into an intravenous dose group of 30 mice (Group 1) and oral dose group of 27 mice (Group 2). Animals in Group 1 received intravenous bolus dose via tail vein at 3 mg/kg and animals in Group 2 received oral solution dose via gavage at 15 mg/kg. Three animals were administered the dose for each time point (intravenous: 10 time points; Oral: 9 time points). Terminal blood samples were collected from each mouse under light ether anesthesia and plasma was separated.

CBC Evaluation Group

A total of 24 mice were divided in to four groups as follows:

| Route | Treatment | No. of animals |
|---|---|---|
| IV | Formulation (3 mg/kg) | 6 |
|  | Vehicle control | 6 |
| Oral | Formulation (15 mg/kg) | 6 |
|  | Vehicle control | 6 |

After 48 h of dosing, approximately 0.5 mL of blood was withdrawn for CBC evaluation. Complete blood count was performed using ADVIA™ 2120 hematology system (Bayer, USA) at Clinical Pathology section, Department of Safety Assessment, Advinus Therapeutics Pvt. Ltd.

Animals in Group 1 were administered an intravenous bolus dose via the tail vein (dosing volume: 6 mL/kg). Animals in Group 2 received oral dose by gavage with an oral dosing needle (dosing volume: 10 mL/kg). Animals in the CBC evaluation group were treated same as above except the animals in control group received vehicle instead of formulation.

Pharmacokinetic group: Predose samples were collected from 3 animals in each group. Following dose administration terminal blood samples were collected at each of the following time points (in triplicate): 0.083 (only for intravenous), 0.25, 0.5, 1, 2, 4, 8, 12 and 24 hours. For each time point, approximately 500 µL of whole blood was withdrawn from the retro orbital sinus and collected in labeled tubes containing dipotassium EDTA as anticoagulant (20 µL of 200 mM K2 EDTA solution per mL of blood). Plasma was separated by centrifuging the whole blood at about 2500 g for 10 minutes at 4° C. within 1 h of sample collection. Separated plasma was stored below minus 50° C. until bioanalysis.

CBC evaluation group: Approximately 500 µL of blood was collected after 48 h after dose administration from all animals in labeled tubes containing lithium heparin (10 IU/mL) as anticoagulant.

Bioanalysis

An LC-MS/MS method was developed and employed for the quantitation of 1H-indole-3-carbaldehyde quinolin-8-yl-hydrazone in the mouse plasma samples. The samples were prepared for analysis following liquid-liquid extraction using amodiaquin as internal standard. The lower limit of quantitation was 1.04 ng/mL.

Pharmacokinetic Analysis

Pharmacokinetic parameters were calculated using non-compartmental analysis tool of WINNONLIN™ Enterprise software (Version 5.1.1). All samples were collected within ±2 minutes of the scheduled time, thus nominal time points were used for pharmacokinetic analysis. Mean plasma concentration at each time point and nominal dose was used to determine pharmacokinetic parameters. Nominal Clearance (CL=Dose/AUC) and volume of distribution at steady state (Vss=MRTinfxCL) was calculated from the animals that were dosed intravenously. The area under the plasma concentration-time curve ($AUC_{0-inf}$) was calculated by linear trapezoidal rule. Peak plasma concentration ($C_{max}$) and time for the peak plasma concentration ($T_{max}$) were directly taken from the observed values. The elimination half-life ($T_{1/2}$) was estimated by linear regression analysis of the terminal phase of the plasma concentration-time profile.

Results

Pharmacokinetics: Plasma concentration-time data of 1H-indole-3-carbaldehyde quinolin-8-ylhydrazone following intravenous and oral administration are presented in Tables 1 and 2, respectively and their summary statistics in Tables 3 and 4. Plasma concentration-time profiles are presented in FIG. 7. The pharmacokinetic parameters are presented in Table 5.

Plasma concentrations were observed till 12 hours following both intravenous and oral administration. Following intravenous administration, 1H-indole-3-carbaldehyde quinolin-8-ylhydrazone undergoes moderate clearance (54.78 mL/min/kg; about 60% of liver blood flow) and has a large volume of distribution (4.28 Ukg; about 6 times of total body water). The half-life is approximately 1.7 hours following intravenous administration. Following oral dosing, maximum concentration of 1H-indole-3-carbaldehyde quinolin-8-ylhydrazone was reached at 1.0 hour post-dose, indicating fast absorption.

The absolute oral solution bioavailability of 1H-indole-3-carbaldehyde quinolin-8-ylhydrazone in male Swiss Albino mouse was approximately 26%.

CBC Evaluation: The individual and mean haematological values are presented in Table 6 and 7. The haematological values of mice treated with intravenous (3 mg/kg) and oral (15 mg/kg) formulation was compared with their respective vehicle control groups. Unpaired t-test was used for statistical comparison.

There was no effect on the haematological parameters except for lower white blood cell count in the formulation treated group following intravenous administration, and lower platelet count in the formulation treated group following oral administration when compared to their corresponding vehicle control group.

TABLE 1

Individual plasma concentration-time data of 1H-indole-3-carbaldehyde quinolin-8-ylhydrazone in male Swiss Albino mouse following intravenous bolus administration (3 mg/kg)

| Individual | Mouse ID | Concentration (ng/mL) |
|---|---|---|
| 0 | 243 | BLQ[a] |
|  | 244 | BLQ |
|  | 245 | BLQ |
| 0.083 | 246 | 2253.61 |
|  | 247 | 1125.73 |
|  | 248 | 75.62 b |
| 0.25 | 249 | 199.60 |
|  | 250 | 307.05 |
|  | 251 | 225.35 |
| 0.5 | 252 | 388.25 |
|  | 253 | 148.82 |
|  | 254 | 339.56 |
| 1 | 255 | 116.46 |
|  | 256 | 184.80 |
|  | 257 | 140.18 |
| 2 | 258 | 71.88 |
|  | 259 | 76.60 |
|  | 260 | 47.02 |
| 4 | 261 | 42.37 |
|  | 262 | 27.25 |
|  | 263 | 38.13 |
| 8 | 264 | 10.11 |
|  | 265 | 5.65 |
|  | 266 | 11.10 |
| 12 | 267 | 1.68 |
|  | 268 | 2.20 |
|  | 269 | BLQ |
| 24 | 270 | BLQ |
|  | 271 | BLQ |
|  | 272 | BLQ |

[a]below limit of quantitation (lower limit of quantitation: 1.04 ng/mL); possible dosing error, value is not considered for pharmacokinetic calculations

TABLE 2

Individual plasma concentration-time data of 1H-indole-3-carbaldehyde quinolin-8-ylhydrazone in male Swiss Albino mouse following oral solution administration (15 mg/kg)

| Time (h) | Mouse ID | Concentration (ng/mL) |
|---|---|---|
| 0 | 273 | BLQ[a] |
|  | 274 | BLQ |
|  | 275 | BLQ |
| 0.25 | 276 | 53.05 |
|  | 277 | 113.38 |
|  | 278 | 254.20 |
| 0.5 | 279 | 96.22 |
|  | 280 | 72.56 |
|  | 281 | 273.76 |
| 1 | 282 | 143.63 |
|  | 283 | 32.21 |
|  | 284 | 422.48 |
| 2 | 285 | 51.85 |
|  | 286 | 95.13 |
|  | 287 | 142.67 |
| 4 | 288 | 185.50 |
|  | 289 | 87.82 |
|  | 290 | 164.88 |
| 8 | 291 | 76.65 |
|  | 292 | 71.29 |
|  | 293 | 78.06 |
| 12 | 294 | 4.05 |
|  | 295 | 11.47 |
|  | 296 | 11.21 |
| 24 | 297 | BLQ |

TABLE 2-continued

Individual plasma concentration-time data of 1H-indole-3-carbaldehyde quinolin-8-ylhydrazone in male Swiss Albino mouse following oral solution administration (15 mg/kg)

| Time (h) | Mouse ID | Concentration (ng/mL) |
|---|---|---|
|  | 298 | BLQ |
|  | 299 | BLQ |

[a]below limit of quantitation (lower limit of quantitation: 1.04 ng/mL)

TABLE 3

Mean plasma concentration-time data of 1H-indole-3-carbaldehyde quinolin-8-ylhydrazone in male Swiss Albino mouse (N = 3) following intravenous bolus administration (3 mg/kg)

| | Concentration (ng/mL) | | |
|---|---|---|---|
| Time (h) | Mean | SD | % CV |
| 0 | BLQ[a] | NA[b] | NA |
| 0.083[c] | 1689.67 | 797.53 | 47 |
| 0.25 | 244.00 | 56.10 | 23 |
| 0.5 | 292.21 | 126.54 | 43 |
| 1 | 147.15 | 34.70 | 24 |
| 2 | 65.17 | 15.89 | 24 |
| 4 | 35.92 | 7.80 | 22 |
| 8 | 8.95 | 2.90 | 32 |
| 12 | 1.29 | 1.15 | 89 |
| 24 | BLQ | NA | NA |

[a]below limit of quantitation (lower limit of quantitation: 1.04 ng/mL);
[b]not applicable;
[c]N = 2

TABLE 4

Mean plasma concentration-time data of 1H-indole-3-carbaldehyde quinolin-8-ylhydrazone in male Swiss Albino mouse (N = 3) following oral solution administration (15 mg/kg)

| | Concentration (ng/mL) | | |
|---|---|---|---|
| Time (h) | Mean | SD | % CV |
| 0 | BLQ a | NA b | NA |
| 0.25 | 140.21 | 103.22 | 74 |
| 0.5 | 147.51 | 109.97 | 75 |
| 1 | 199.44 | 201.03 | 101 |
| 2 | 96.55 | 45.43 | 47 |
| 4 | 146.07 | 51.49 | 35 |
| 8 | 75.33 | 3.57 | 5 |
| 12 | 8.91 | 4.21 | 47 |
| 24 | BLQ | NA | NA | a below limit of quantitation (lower limit of quantitation: 1.04 ng/mL);
b not applicable

TABLE 5

Pharmacokinetic parameters of 1H-indole-3-carbaldehyde quinolin-8-ylhydrazone in male Swiss Albino mouse (N = 3) following intravenous bolus (3 mg/kg) and oral solution administration (15 mg/kg)

| Route | $T_{max}$ (h) | $C_{max}$ (ng/mL) | $AUC_{0-t}$ (ng·h/mL) | $AUC_{O-Inf}$ (ng·h/mL) | $T_{1/2}$ (h) | CL (mL/min/kg) | Vds. (L/kg) | F[a] (%) |
|---|---|---|---|---|---|---|---|---|
| IV (3 mg/kg) | 0.083[b] | 1689.67 | 909.38 | 912.79 | 1.67 | 54.78 | 4.28 | — |
| Oral (15 mg/kg) | 1.0 | 199.44 | 1142.13 | 1174.70 | 1.98 | — | — | 26 |

[a]absolute bioavailability, F = $(AUC_{0-inf})_{oral}$ × $dose_{iv}/(AUC_{0-int})_{iv}$ × $dose_{oral}$;
[b]first sampling point

Example 9

Bioanalytical Analysis

The objective of the bioanalytical phase was to determine the plasma concentration of 1H-indole-3-carbaldehyde quinolin-8-ylhydrazone (ICQH) in male Swiss albino mice plasma samples from Study Plan N0178.

In vivo part of Study: The animals were divided into two groups: Group 1 (Mouse ID 243 through 272), Group 2 (Mouse ID 273 through 299). Group 1 was dosed intravenously and Group 2 was dosed orally. A total of 30 plasma samples were collected from Group 1 animals. At each of the predetermined time points, plasma samples were collected from 3 animals. Similarly from Group 2 a total of 27 plasma samples were collected. A total of 57 plasma samples were collected as per the study plan. All plasma samples were stored below minus 70° C. in the deep freezer of DMPK and Clinical Pharmacology department. An LC-MS/MS method for the estimation of 1H-indole-3-carbaldehyde quinolin-8-ylhydrazone (ICQH) in Swiss albino mouse plasma was developed and partially validated for precision and accuracy. Specifically, ICQH was extracted from mouse plasma samples by liquid-liquid (methyl-tert-butyl ether) extraction. An aliquot of final processed sample was analyzed by combined reversed phase liquid chromatography tandem mass spectrometry by multiple reaction monitoring and positive ionization mode.

Analytical batch contained one set of calibration standards, blank plasma, blank with internal standard and three sets of QC samples, which are interspersed with study samples. Analysis of four samples were repeated with one set of calibration standards includes blank plasma, blank with internal standard and two sets of QC samples.

Data evaluation and acceptance criteria: Peak area ratios of analyte were calculated by peak area of analyte/internal standard. The concentration of unknown were calculated based on the following equation using regression analysis of spiked calibration standard with the reciprocal of the square of test item concentration as a weighting factor (1/concentration$^2$).

$$y = mx + c$$

where, y=peak area ratio of analyte over internal standard; m=slope of the calibration curve; x=concentration of analyte of interest (ng/mL); and c=Y axis intercept of the calibration curve.

The samples were analyzed in two analytical runs. Final accepted concentrations of the mouse plasma samples are given in Table 7. Four study samples were reanalyzed for pharmacokinetic reasons. Details of reanalyzed samples are tabulated in Table 8.

Peak area ratio of the individual calibration standards were fitted according to the described model. The intercept was close to zero and the square regression coefficient was close to 1 having accuracy between 88.70 to 116.14.

TABLE 7

Plasma concentration (ng/mL) data of 1 H-indole-3-carbaldehyde quinolin-8-ylhydrazone (ICQH) in study samples

| Time (h) | Mouse ID | Intravenous concentration | Mouse ID | Oral concentrations |
|---|---|---|---|---|
| 0.00 | 243 | BLQ$^a$ | 273 | BLQ |
|  | 244 | BLQ | 274 | BLQ |
|  | 245 | BLQ | 275 | BLQ |
| 0.08 | 246 | 2253.61 |  | NA$^b$ |
|  | 247 | 1125.73 |  |  |
|  | 248 | 75.62 |  |  |
| 0.25 | 249 | 199.60 | 276 | 53.05 |
|  | 250 | 307.05 | 277 | 113.38 |
|  | 251 | 225.35 | 278 | 254.20 |
| 0.50 | 252 | 388.25 | 279 | 96.22 |
|  | 253 | 148.82 | 280 | 72.56 |
|  | 254 | 339.56 | 281 | 273.76 |
| 1.00 | 255 | 184.80 | 282 | 143.63 |
|  | 256 | 116.46 | 283 | 32.21 |
|  | 257 | 140.18 | 284 | 422.48 |
| 2.00 | 258 | 71.88 | 285 | 51.85 |
|  | 259 | 76.60 | 286 | 95.13 |
|  | 260 | 47.02 | 287 | 142.67 |
| 4.00 | 261 | 42.37 | 288 | 185.50 |
|  | 262 | 27.25 | 289 | 87.82 |
|  | 263 | 38.13 | 290 | 164.88 |
| 8.00 | 264 | 10.11 | 291 | 76.65 |
|  | 265 | 5.65 | 292 | 71.29 |
|  | 266 | 11.10 | 293 | 78.06 |
| 12.00 | 267 | 1.68 | 294 | 4.05 |
|  | 268 | 2.20 | 295 | 11.47 |
|  | 269 | BLQ | 296 | 11.21 |
| 24.00 | 270 | BLQ | 297 | BLQ |
|  | 271 | BLQ | 298 | BLQ |
|  | 272 | BLQ | 299 | BLQ |

$^a$below limit of quantitation (LLOQ = 1.04 ng/mL);
$^b$not applicable

TABLE 8

Repeat analysis summary of 1H-indole-3-carbaldehyde quinolin-8-ylhydrazone (ICQH) in study samples

| Sl. No. | Sample Name | Initial conc. (ng/mL) | Repeated conc. (ng/mL) | Accepted conc. (ng/mL) |
|---|---|---|---|---|
| 1 | ICQH-MP-IV-243-0 HR | 1.65 | BLQ a | BLQ b |
| 2 | ICQH-MP-IV-248-0.083 HR | 47.33 | 75.62 | 75.62 c |
| 3 | ICQH-MP-IV-249-0.25 HR | 130.42 | 199.60 | 199.60 c |
| 4 | ICQH-MP-IV-251-0.25 HR | 132.16 | 225.35 | 225.35 c | a below limit of quantitation (LLOQ = 1.04 ng/mL);
b analytical repeat, repeat value accepted; pharmacokinetic anomaly (acceptance criteria: If the difference between the original and repeat value is less than 20%, then original is accepted; if it is in between 20 to 30%, then average value is accepted; if the difference is greater than 30%, then the value was reported based on discretion.

REFERENCES

Ackermann, G. E., and B. H. Paw. 2003. Zebrafish: a genetic model for vertebrate organogenesis and human disorders. *Front Biosci* 8:d1227-1253.

Ater, J. C. 2005. Deregulated NOTCH signaling in acute T-cell lymphoblastic leukemia/lymphoma: new insights, questions, and opportunities. *Int J Hematol* 82:295-301.

Bennett, C. M., Z. R. Rogers, D. D. Kinnamon, J. B. Bussel, D. H. Mahoney, T. C. Abshire, H. Sawaf, T. B. Moore, M. L. Loh, B. E. Glader, M. C. McCarthy, B. U. Mueller, T. A. Olson, A. N. Lorenzana, W. C. Mentzer, G. R. Buchanan, H. A. Feldman, and E. J. Neufeld. 2006. Prospective phase 1/2 study of rituximab in childhood and adolescent chronic immune thrombocytopenic purpura. *Blood* 107:2639-2642.

Berube, C., L. M. Boucher, W. Ma, A. Wakeham, L. Salmena, R. Hakem, W. C. Yeh, T. W. Mak, and S. Benchimol. 2005. Apoptosis caused by p53-induced protein with death domain (PIDD) depends on the death adapter protein RAIDD. *Proc Natl Acad Sci U S A* 102:14314-14320.

Chhabra, A., S. Mehrotra, N. G. Chakraborty, D. I. Dorsky, and B. Mukherji. 2006. Activation-induced cell death of human melanoma specific cytotoxic T lymphocytes is mediated by apoptosis-inducing factor. *Eur J Immunol* 36:3167-3174.

Chipuk, J. E., and D. R. Green. 2006. Dissecting p53-dependent apoptosis. *Cell Death Differ* 13:994-1002.

Clift, R. A., and R. Storb. 1996. Marrow transplantation for CML: the Seattle experience. *Bone Marrow Transplant* 17 Suppl 3:S1-3.

Cvetkovic, R. S., and C. M. Perry. 2006. Rituximab: a review of its use in non-Hodgkin's lymphoma and chronic lymphocytic leukaemia. *Drugs* 66:791-820.

Druker, B. J., F. Guilhot, S. G. O'Brien, I. Gathmann, H. Kantarjian, N. Gattermann, M. W. Deininger, R. T. Silver, J. M. Goldman, R. M. Stone, F. Cervantes, A. Hochhaus, B. L. Powell, J. L. Gabrilove, P. Rousselot, J. Reiffers, J. J. Cornelissen, T. Hughes, H. Agis, T. Fischer, G. Verhoef, J. Shepherd, G. Saglio, A. Gratwohl, J. L. Nielsen, J. P. Radich, B. Simonsson, K. Taylor, M. Baccarani, C. So, L. Letvak, and R. A. Larson. 2006. Five-year follow-up of patients receiving imatinib for chronic myeloid leukemia. *N Engl J Med* 355:2408-2417.

Druker, B. J., S. Tamura, E. Buchdunger, S. Ohno, G. M. Segal, S. Fanning, J. Zimmermann, and N. B. Lydon. 1996. Effects of a selective inhibitor of the Abl tyrosine kinase on the growth of Bcr-Abl positive cells. *Nat Med* 2:561-566.

Esteve, P., N. Embade, R. Perona, B. Jimenez, L. del Peso, J. Leon, M. Arends, T. Miki, and J. C. Lacal. 1998. Rho-regulated signals induce apoptosis in vitro and in vivo by a p53-independent, but Bcl2 dependent pathway. *Oncogene* 17:1855-1869.

Goldberg, J. M., L. B. Silverman, D. E. Levy, V. K. Dalton, R. D. Gelber, L. Lehmann, H. J. Cohen, S. E. Sallan, and B. L. Asselin. 2003. Childhood T-cell acute lymphoblastic leukemia: the Dana-Farber Cancer Institute acute lymphoblastic leukemia consortium experience. *J Clin Oncol* 21:3616-3622.

Gozuacik, D., and A. Kimchi. 2007. Autophagy and cell death. *Curr Top Dev Biol* 78:217-245.

Grabher, C., H. von Boehmer, and A. T. Look. 2006. Notch 1 activation in the molecular pathogenesis of T-cell acute lymphoblastic leukaemia. *Nat Rev Cancer* 6:347-359.

Guo, Z., M. Dose, D. Kovalovsky, R. Chang, J. O'Neil, A. T. Look, H. von Boehmer, K. Khazaie, and F. Gounari. 2007. {beta}-Catenin stabilization stalls the transition from Double-Positive to Single Positive stage and predisposes thymocytes to malignant transformation. *Blood*.

Hatanaka, Y., and Y. Sadakane. 2002. Photoaffinity labeling in drug discovery and developments: chemical gateway for entering proteomic frontier. *Curr Top Med Chem* 2:271-288.

Heidel, F., D. B. Lipka, C. von Auer, C. Huber, I. Scharrer, and G. Hess. 2007. Addition of rituximab to standard therapy improves response rate and progression-free survival in relapsed or refractory thrombotic thrombocytopenic purpura and autoimmune haemolytic anaemia. *Thromb Haemost* 97:228-233.

Holler, N., R. Zaru, O. Micheau, M. Thome, A. Attinger, S. Valitutti, J. L. Bodmer, P. Schneider, B. Seed, and J. Tschopp. 2000. Fas triggers an alternative, caspase-8-independent cell death pathway using the kinase RIP as effector molecule. *Nat Immunol* 1:489-495.

Jaattela, M., and J. Tschopp. 2003. Caspase-independent cell death in T lymphocytes. *Nat Immunol* 4:416-423.

Langenau, D. M., A. A. Ferrando, D. Traver, J. L. Kutok, J. P. Hezel, J. P. Kanki, L. I. Zon, A. T. Look, and N. S. Trede. 2004. In vivo tracking of T cell development, ablation, and engraftment in transgenic zebrafish. *Proc Natl Acad Sci USA* 101:7369-7374.

Langenau, D. M., C. Jette, S. Berghmans, T. Palomero, J. P. Kanki, J. L. Kutok, and A. T. Look. 2005. Suppression of apoptosis by bcl-2 overexpression in lymphoid cells of transgenic zebrafish. *Blood* 105:3278-3285.

Langenau, D. M., D. Traver, A. A. Ferrando, J. L. Kutok, J. C. Aster, J. P. Kanki, S. Lin, E. Prochownik, N. S. Trede, L. I. Zon, and A. T. Look. 2003. Myc-induced T cell leukemia in transgenic zebrafish. *Science* 299:887-890.

Lin, Y., W. Ma, and S. Benchimol. 2000. Pidd, a new death-domain-containing protein, is induced by p53 and promotes apoptosis. *Nat Genet.* 26:122-127.

Murphey, R. D., H. M. Stern, C. T. Straub, and L. I. Zon. 2006. A chemical genetic screen for cell cycle inhibitors in zebrafish embryos. *Chem Biol Drug Des* 68:213-219.

Nesbit, M. E., Jr., J. D. Buckley, S. A. Feig, J. R. Anderson, B. Lampkin, I. D. Bernstein, T. H. Kim, S. Piomelli, J. H. Kersey, P. F. Coccia, and et al. 1994. Chemotherapy for induction of remission of childhood acute myeloid leukemia followed by marrow transplantation or multiagent chemotherapy: a report from the Childrens Cancer Group. *J Clin Oncol* 12:127-135.

Newton, K., C. Kurts, A. W. Harris, and A. Strasser. 2001. Effects of a dominant interfering mutant of FADD on signal transduction in activated T cells. *Curr Biol* 11:273-276.

O'Connor, L., A. W. Harris, and A. Strasser. 2000. CD95 (Fas/APO-1) and p53 signal apoptosis independently in diverse cell types. *Cancer Res* 60:1217-1220.

Oeffinger, K. C., A. C. Mertens, C. A. Sklar, T. Kawashima, M. M. Hudson, A. T. Meadows, D. L. Friedman, N. Marina, W. Hobbie, N. S. Kadan-Lottick, C. L. Schwartz, W. Leisenring, and L. L. Robison. 2006. Chronic health conditions in adult survivors of childhood cancer. *N Engl J Med* 355:1572-1582.

Peterson, R. T., B. A. Link, J. E. Dowling, and S. L. Schreiber. 2000. Small molecule developmental screens reveal the logic and timing of vertebrate development. *Proc Natl Acad Sci USA* 97:12965-12969.

Peterson, R. T., S. Y. Shaw, T. A. Peterson, D. J. Milan, T. P. Zhong, S. L. Schreiber, C. A. MacRae, and M. C. Fishman. 2004. Chemical suppression of a genetic mutation in a zebrafish model of aortic coarctation. *Nat Biotechnol* 22:595-599.

Randolph, T. R. 2000. Acute promyelocytic leukemia (AML-M3)—Part 1: Pathophysiology, clinical diagnosis, and differentiation therapy. *Clin Lab Sci* 13:98-105.

Reiter, A., M. Schrappe, W. D. Ludwig, W. Hiddemann, S. Sauter, G. Henze, M. Zimmermann, F. Lampert, W. Havers, D. Niethammer, and et al. 1994. Chemotherapy in 998 unselected childhood acute lymphoblastic leukemia patients. Results and conclusions of the multicenter trial ALL-BFM 86. *Blood* 84:3122-3133.

Rndolph, T. R. 2000. Acute promyelocytic leukemia (AML-M3)—Part 2: Molecular defect, DNA diagnosis, and proposed models of leukemogenesis and differentiation therapy. *Clin Lab Sci* 13:106-116.

Schmitt, C. A., J. S. Fridman, M. Yang, E. Baranov, R. M. Hoffman, and S. W. Lowe. 2002. Dissecting p53 tumor suppressor functions in vivo. *Cancer Cell* 1:289-298.

Seddon, B., and R. Zamoyska. 2002. TCR signals mediated by Src family kinases are essential for the survival of naive T cells. *J Immunol* 169:2997-3005.

Segmaier, K., S. M. Corsello, K. N. Ross, J. S. Wong, D. J. Deangelo, and T. R. Golub. 2005. Gefitinib induces myeloid differentiation of acute myeloid leukemia. *Blood* 106:2841-2848.

Shepard, J. L., J. F. Amatruda, H. M. Stern, A. Subramanian, D. Finkelstein, J. Ziai, K. R. Finley, K. L. Pfaff, C. Hersey, Y. Zhou, B. Barut, M. Freedman, C. Lee, J. Spitsbergen, D. Neuberg, G. Weber, T. R. Golub, J. N. Glickman, J. L. Kutok, J. C. Aster, and L. I. Zon. 2005. A zebrafish bmyb mutation causes genome instability and increased cancer susceptibility. *Proc Natl Acad Sci USA* 102:13194-13199.

Spring, D. R. 2005. Chemical genetics to chemical genomics: small molecules offer big insights. *Chem Soc Rev* 34:472-482.

Stern, H. M., R. D. Murphey, J. L. Shepard, J. F. Amatruda, C. T. Straub, K. L. Pfaff, G. Weber, J. A. Tallarico, R. W. King, and L. I. Zon. 2005. Small molecules that delay S phase suppress a zebrafish bmyb mutant. *Nat Chem Biol* 1:366-370.

Strasser, A., A. W. Harris, T. Jacks, and S. Cory. 1994. DNA damage can induce apoptosis in proliferating lymphoid cells via p53-independent mechanisms inhibitable by Bcl-2. *Cell* 79:329-339.

Tejeda, M., D. Gaal, O. Csuka, and G. Keri. 2005. Growth inhibitory effect of the somatostatin structural derivative (TT-232) on leukemia models. *Anticancer Res* 25:325-330.

Tolomeo, M., and D. Simoni. 2002. Drug resistance and apoptosis in cancer treatment: development of new apoptosis-inducing agents active in drug resistant malignancies. *Curr Med Chem Anticancer Agents* 2:387-401.

Trede, N. S., D. M. Langenau, D. Traver, A. T. Look, and L. I. Zon. 2004. The use of zebrafish to understand immunity. *Immunity* 20:367-379.

Trede, N., J. Medenbach, A. Damianov, L.-H. Hung, G. Weber, B. Paw, Y. Zhou, C. Hersey, A. Zapata, M. Keefe, B. Barut, A. Stuart, T. Katz, C. Amemiya, L. Zon, and A. Bindereif 2007. Organ development in zebrafish linked to network of coregulated splicing factors. *Proc. Natl. Acad. Sci.* in press.

Wahlstrom, J. L., M. A. Randall, Jr., J. D. Lawson, D. E. Lyons, W. F. Siems, G. J. Crouch, R. Barr, K. C. Facemyer, and C. R. Cremo. 2003. Structural model of the regulatory domain of smooth muscle heavy meromyosin. *J Biol Chem* 278:5123-5131.

Walensky, L. D., A. L. Kung, I. Escher, T. J. Malia, S. Barbuto, R. D. Wright, G. Wagner, G. L. Verdine, and S. J. Korsmeyer. 2004. Activation of apoptosis in vivo by a hydrocarbon-stapled BH3 helix. *Science* 305:1466-1470.

Wang, H., L. J. Pierce, and G. J. Spangrude. 2005. Lymphoid potential of primitive bone marrow progenitors evaluated in vitro. *Ann N Y Acad Sci* 1044:210-219.

Wang, H., L. J. Pierce, and G. J. Spangrude. 2006. Distinct roles of IL-7 and stem cell factor in the OP9-DL1 T-cell differentiation culture system. *Exp Hematol* 34:1730-1740.

Weng, A. P., A. A. Ferrando, W. Lee, J. P. t. Morris, L. B. Silverman, C. Sanchez-Irizarry, S. C. Blacklow, A. T. Look, and J. C. Aster. 2004. Activating mutations of NOTCH1 in human T cell acute lymphoblastic leukemia. *Science* 306:269-271.

Weng, A. P., J. M. Millholland, Y. Yashiro-Ohtani, M. L. Arcangeli, A. Lau, C. Wai, C. Del Bianco, C. G. Rodriguez, H. Sai, J. Tobias, Y. Li, M. S. Wolfe, C. Shachaf, D. Felsher, S. C. Blacklow, W. S. Pear, and J. C. Aster. 2006. c-Myc is an important direct target of Notch1 in T-cell acute lymphoblastic leukemia/lymphoma. *Genes Dev* 20:2096-2109.

Zon, L. I., and R. T. Peterson. 2005. In vivo drug discovery in the zebrafish. *Nat Rev Drug Discov* 4:35-44.

What is claimed is:

1. A method of modulating T-cell activity, comprising administering to a subject diagnosed with T-cell acute lymphocytic leukemia (T-ALL) a composition comprising a therapeutically effective amount of a compound having a formula:

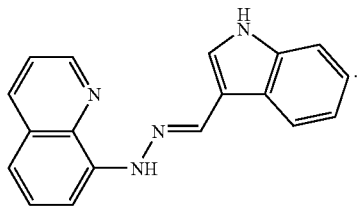

or a pharmaceutically acceptable salt thereof.

2. The method of claim 1, wherein the composition is administered prior to treatment with an approved chemotherapeutic agent.

3. The method of claim 1, wherein the subject has been diagnosed with a T-cell acute lymphocytic leukemia (T-ALL) prior to administration.

4. The method of claim 1, further comprising the step of identifying in the subject a need for treatment of a T-cell acute lymphocytic leukemia (T-ALL).

5. The method of claim 1, further comprising the step of treatment with an approved chemotherapeutic agent.

6. The method of claim 1, wherein administration is performed within one week of T-ALL diagnosis.

7. The method of claim 1, wherein administration is performed as an alternative to conventional chemotherapy.

8. The method of claim 1, wherein the subject is human.

9. The method of claim 1, wherein the diagnosed T-ALL is refractory T-ALL or relapsed T-ALL.

10. The method of claim 1, wherein the subject is also in need for treatment for one or more of rheumatoid arthritis, multiple sclerosis, and graft-vs-host disease (GvHD).

11. The method of claim 1, wherein the composition further comprises one or more additional active ingredients selected from antimicrobial agents, anti-inflammatory agents, and anesthetics.

12. The method of claim 1, wherein administration is oral administration.

13. The method of claim 1, wherein administration is performed intravenously, intraperitoneally, intramuscularly, subcutaneously, intracavity, or transdermally.

14. The method of claim 1, wherein the compound is present in the forma of a pharmaceutically acceptable salt.

* * * * *